United States Patent
Lai et al.

(10) Patent No.: US 9,347,107 B2
(45) Date of Patent: May 24, 2016

(54) VECTOR CONTAINING MULTIPLE NUCLEOTIDE SEQUENCES FOR THE EXPRESSION OF ENZYMES

(71) Applicants: Norman Z Lai, North Potomac, MD (US); Fred Nyberg, Uppsala (SE); Hung Mak, North Point (HK)

(72) Inventors: Norman Z Lai, North Potomac, MD (US); Fred Nyberg, Uppsala (SE); Hung Mak, North Point (HK)

( * ) Notice: Subject to any disclaimer, the term of this patent is extended or adjusted under 35 U.S.C. 154(b) by 96 days.

(21) Appl. No.: 14/286,931

(22) Filed: May 23, 2014

(65) Prior Publication Data

US 2014/0349370 A1    Nov. 27, 2014

Related U.S. Application Data

(60) Provisional application No. 61/826,545, filed on May 23, 2013.

(51) Int. Cl.
*C12N 9/24* (2006.01)

(52) U.S. Cl.
CPC ....... *C12Y 302/01045* (2013.01); *C12N 9/2402* (2013.01); *C07K 2319/10* (2013.01); *C07K 2319/33* (2013.01); *C07K 2319/50* (2013.01)

(58) Field of Classification Search
None
See application file for complete search history.

(56) References Cited

PUBLICATIONS

Koeduka et al. (Proc. Natl. Acad. Sci. U.S.A. 103 (26), 10128-10133 (2006)).*

* cited by examiner

*Primary Examiner* — Suzanne M Noakes
*Assistant Examiner* — Jae W Lee
(74) *Attorney, Agent, or Firm* — Anova Law Group, PLLC

(57) ABSTRACT

An expression vector is provided. The vector includes a promoter configured to drive the expression of the transgene in the cell. The vector also includes a tag sequence encoding a tag peptide directing the protein of the expressed transgene to a pre-determined location. The vector further includes a cleavage sequence encoding a peptide that is recognizable by a protease and a marker gene configured to encoding a protein to indicate the expression of the transgene.

15 Claims, 6 Drawing Sheets

SEQUENCE LISTING

```
<160> NUMBER OF SEQ ID NOS: 25

<210> SEQ ID NO 1
<211> LENGTH: 11
<212> TYPE: PRT
<213> ORGANISM: Drosophila

<400> SEQUENCE: 1

Arg Gln Ile Lys Ile Trp Phe Gln Asn Arg Arg
1               5                   10

<210> SEQ ID NO 2
<211> LENGTH: 11
<212> TYPE: PRT
<213> ORGANISM: Homo sapiens

<400> SEQUENCE: 2

Tyr Gly Arg Lys Lys Arg Arg Gln Arg Arg Arg
1               5                   10

<210> SEQ ID NO 3
<211> LENGTH: 300
<212> TYPE: PRT
<213> ORGANISM: Homo sapiens

<400> SEQUENCE: 3

Met Thr Ser Arg Arg Ser Val Lys Ser Gly Pro Arg Glu Val Pro Arg
1               5                   10                  15
```

Asp Glu Tyr Glu Asp Leu Tyr Tyr Thr Pro Ser Ser Cys Met Ala Ser
                20                  25                  30

Pro Asp Ser Pro Pro Asp Thr Ser Arg Arg Gly Ala Leu Gln Thr Arg
        35                  40                  45

Ala Arg Pro Arg Gly Glu Val Arg Phe Val Gln Tyr Asp Glu Ser Asp
 50                  55                  60

Tyr Ala Leu Tyr Gly Gly Ser Ser Glu Asp Glu His Pro Glu
 65                  70                  75                  80

Val Pro Arg Thr Arg Arg Pro Val Ser Gly Ala Val Leu Ser Ala Pro
                85                  90                  95

Gly Pro Ala Arg Ala Pro Pro Pro Ala Gly Ser Gly Gly Ala Gly
                100                 105                 110

Arg Thr Pro Thr Thr Ala Pro Arg Ala Pro Arg Thr Gln Arg Val Ala
                115                 120                 125

Thr Lys Ala Pro Ala Ala Pro Ala Ala Glu Thr Thr Arg Gly Arg Lys
130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
                180                 185                 190

Val Ala Gly Phe Asn Lys Arg Val Phe Cys Ala Ala Val Gly Arg Leu
                195                 200                 205

Ala Ala Met His Ala Arg Met Ala Ala Val Gln Leu Trp Asp Met Ser
                210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Ile Gln Arg Ala Asn
                245                 250                 255

Glu Leu Val Asn Pro Asp Val Val Gln Asp Val Asp Ala Ala Thr Ala
                260                 265                 270

Thr Arg Gly Arg Ser Ala Ala Ser Arg Pro Thr Glu Arg Pro Arg Ala
                275                 280                 285

Pro Ala Arg Ser Ala Ser Arg Pro Arg Arg Pro Val
290                 295                 300

<210> SEQ ID NO 4
<211> LENGTH: 20
<212> TYPE: PRT
<213> ORGANISM: Foot and Mouth Disease Virus

<400> SEQUENCE: 4

Leu Leu Asn Phe Asp Leu Leu Lys Leu Leu Ala Gly Asp Val Glu Ser
1               5                   10                  15

Asn Pro Cys Pro
            20

<210> SEQ ID NO 5
<211> LENGTH: 90
<212> TYPE: PRT
<213> ORGANISM: Bubalus bubalis

<400> SEQUENCE: 5

Met Asp Ser Lys Gly Ser Ser Gln Lys Gly Ser Arg Leu Leu Leu Leu
1               5                   10                  15

```
Leu Val Val Ser Asn Leu Leu Leu Cys Gln Cys Val Ser Thr Pro
            20                  25                  30

Val Cys Pro Asn Gly Pro Gly Asn Cys Gln Val Ser Leu Arg Asp Leu
        35                  40                  45

Phe Asp Arg Ala Val Met Val Ser His Tyr Ile His Asp Leu Ser Ser
 50                  55                  60

Glu Met Phe Asn Glu Phe Asp Lys Arg Tyr Ala Gln Gly Lys Gly Phe
 65                  70                  75                  80

Ile Thr Met Ala Leu Asn Ser Cys His Thr
                85                  90

<210> SEQ ID NO 6
<211> LENGTH: 43
<212> TYPE: PRT
<213> ORGANISM: Homo sapiens

<400> SEQUENCE: 6

His His Ser Asp Glu Ser Asp Glu Leu Val Thr Asp Phe Pro Thr Asp
 1               5                  10                  15

Leu Pro Ala Thr Glu Val Phe Thr Pro Val Val Pro Thr Val Asp Thr
            20                  25                  30

Tyr Asp Gly Arg Gly Asp Ser Val Val Tyr Gly
        35                  40

<210> SEQ ID NO 7
<211> LENGTH: 41
<212> TYPE: PRT
<213> ORGANISM: Homo sapiens

<400> SEQUENCE: 7

Cys Ser Ile Pro Val Cys Gly Gln Asp Gln Val Thr Val Ala Met Thr
 1               5                  10                  15

Pro Arg Ser Glu Gly Ser Ser Val Asn Leu Ser Pro Pro Leu Glu Gln
            20                  25                  30

Cys Val Pro Asp Arg Gly Gln Gln Tyr
        35                  40

<210> SEQ ID NO 8
<211> LENGTH: 23
<212> TYPE: PRT
<213> ORGANISM: Artificial sequence
<220> FEATURE:
<223> OTHER INFORMATION: synthetic sequence

<400> SEQUENCE: 8

Gln Thr Leu Asn Phe Asp Leu Leu Lys Leu Ala Gly Asp Val Glu Ser
 1               5                  10                  15

Asn Pro Gly Pro Gly Asn Ser
            20

<210> SEQ ID NO 9
<211> LENGTH: 69
<212> TYPE: DNA
<213> ORGANISM: Artificial sequence
<220> FEATURE:
<223> OTHER INFORMATION: synthetic sequence

<400> SEQUENCE: 9
cagactttga attttgacct tctcaagttg gcgggagacg tcgagtccaa ccctgggccc    60
gggaattct                                                           69
```

<210> SEQ ID NO 10
<211> LENGTH: 2139
<212> TYPE: DNA
<213> ORGANISM: Homo sapiens

<400> SEQUENCE: 10

| | | | | | |
|---|---|---|---|---|---|
| atggagtttt | caagtccttc | cagagaggaa | tgtcccaagc | ctttgagtag | ggtaagcatc | 60 |
| atggctggca | gcctcacagg | attgcttcta | cttcaggcag | tgtcgtgggc | atcaggtgcc | 120 |
| cgcccctgca | tccctaaaag | cttcggctac | agctcggtgg | tgtgtgtctg | caatgccaca | 180 |
| tactgtgact | cctttgaccc | cccgaccttt | cctgcccttg | gtaccttcag | ccgctatgag | 240 |
| agtacacgca | gtgggcgacg | gatggagctg | agtatggggc | ccatccaggc | taatcacacg | 300 |
| ggcacaggcc | tgctactgac | cctgcagcca | gaacagaagt | tccagaaagt | gaagggattt | 360 |
| ggagggggcca | tgacagatgc | tgctgctctc | aacatccttg | ccctgtcacc | ccctgcccaa | 420 |
| aatttgctac | ttaaatcgta | cttctctgaa | gaaggaatcg | gatataacat | catccgggta | 480 |
| cccatggcca | gctgtgactt | ctccatccgc | acctacacct | atgcagacac | ccctgatgat | 540 |
| ttccagttgc | acaacttcag | cctcccagag | gaagatacca | agctcaagat | acccctgatt | 600 |
| caccgagccc | tgcagttggc | ccagcgtccc | gtttcactcc | ttgccagccc | ctggacatca | 660 |
| cccacttggc | tcaagaccaa | tggagcggtg | aatgggaagg | ggtcactcaa | gggacagccc | 720 |
| ggagacatct | accaccagac | ctgggccaga | tactttgtga | agttcctgga | tgcctatgct | 780 |
| gagcacaagt | tacagttctg | ggcagtgaca | gctgaaaatg | agccttctgc | tgggctgttg | 840 |
| agtggatacc | ccttccagtg | cctgggcttc | accccctgaac | atcagcgaga | cttcattgcc | 900 |
| cgtgacctag | gtcctaccct | cgccaacagt | actcaccaca | atgtccgcct | actcatgctg | 960 |
| gatgaccaac | gcttgctgct | gccccactgg | gcaaaggtgg | tactgacaga | cccagaagca | 1020 |
| gctaaatatg | ttcatggcat | tgctgtacat | tggtacctgg | actttctggc | tccagccaaa | 1080 |
| gccaccctag | gggagacaca | ccgcctgttc | cccaacacca | tgctctttgc | ctcagaggcc | 1140 |
| tgtgtgggct | ccaagttctg | ggagcagagt | gtgcggctag | ctcctgggat | cgagggatg | 1200 |
| cagtacagcc | acagcatcat | cacgaacctc | ctgtaccatg | tggtcggctg | gaccgactgg | 1260 |
| aaccttgccc | tgaaccccga | aggaggaccc | aattgggtgc | gtaactttgt | cgacagtccc | 1320 |
| atcattgtag | acatccaccaa | ggacacgttt | tacaaacagc | ccatgttcta | ccaccttggc | 1380 |
| cacttcagca | agttcattcc | tgagggctcc | cagagagtgg | ggctggttgc | cagtcagaag | 1440 |
| aacgacctgg | acgcagtggc | actgatgcat | cccgatggct | ctgctgttgt | ggtcgtgcta | 1500 |
| aaccgctcct | ctaaggatgt | gcctcttacc | atcaaggatc | ctgctgtggg | cttcctggag | 1560 |
| acaatctcac | ctggctactc | cattcacacc | tacctgtggc | gtcgccagtg | gagcagatac | 1620 |
| tcaaggaggc | actgggctca | gcctgggcat | agggacagag | tcagctcaca | cgctgtctgt | 1680 |
| gacagagggc | acagcagggc | cagtgtgagc | ttacagcgac | gtaagcccag | ggcaatggt | 1740 |
| ttgggtgact | cactttcccc | tctaggcggt | gcccaggggc | tggaggcccc | tagaaaaaga | 1800 |
| tcagtaagcc | ccagtgtccc | cccagccccc | atgcttatga | catgcgctgt | gtgctgcttg | 1860 |
| cttttggaaac | tgggcctggg | tccaggccta | ggggctcact | gtccgtacaa | acacaagatc | 1920 |
| agggctgagg | gtaaggaaaa | gaagagacta | ggaaagctgg | gcccaaaact | ggagactgtt | 1980 |
| tgtcttttcct | ggagatgcag | aactgggccc | gtggagcagc | agtgtcagca | tcagggcgga | 2040 |
| agccttaaag | cagcagcggg | tgtgcccagg | cacccagatg | attcctatgg | caccagccag | 2100 | gaaaaatggc agctcttaaa ggagaaaatg tttgagccc                                2139

<210> SEQ ID NO 11
<211> LENGTH: 713
<212> TYPE: PRT
<213> ORGANISM: Homo sapiens

<400> SEQUENCE: 11

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
        50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365
```

```
Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Gly
            405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
                435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp Arg Arg Gln Trp Ser Arg Tyr Ser Arg Arg His
    530                 535                 540

Trp Ala Gln Pro Gly His Arg Asp Arg Val Ser Ser His Ala Val Cys
545                 550                 555                 560

Asp Arg Gly His Ser Arg Ala Ser Val Ser Leu Gln Arg Arg Lys Pro
                565                 570                 575

Arg Gly Asn Gly Leu Gly Asp Ser Leu Ser Pro Leu Gly Gly Ala Gln
            580                 585                 590

Gly Leu Glu Ala Pro Arg Lys Arg Ser Val Ser Pro Ser Val Pro Pro
    595                 600                 605

Ala Pro Met Leu Met Thr Cys Ala Val Cys Cys Leu Leu Trp Lys Leu
    610                 615                 620

Gly Leu Gly Pro Gly Leu Gly Ala His Cys Pro Tyr Lys His Lys Ile
625                 630                 635                 640

Arg Ala Glu Gly Lys Glu Lys Lys Arg Leu Gly Lys Leu Gly Pro Lys
                645                 650                 655

Leu Glu Thr Val Cys Leu Ser Trp Arg Cys Arg Thr Gly Pro Val Glu
            660                 665                 670

Gln Gln Cys Gln His Gln Gly Gly Ser Leu Lys Ala Ala Ala Gly Val
    675                 680                 685

Pro Arg His Pro Asp Asp Ser Tyr Gly Thr Ser Gln Glu Lys Trp Gln
    690                 695                 700

Leu Leu Lys Glu Lys Met Phe Glu Pro
705                 710

<210> SEQ ID NO 12
<211> LENGTH: 789
<212> TYPE: DNA
<213> ORGANISM: Proteus sp.

<400> SEQUENCE: 12
atgccaacta catatccaat tgttttagtt catggtctat ctggttttga taatgtcgtc    60
ggttatcctt attttatgg catcgcggat gccttagaaa aggatggtca taaagttttt    120
actgcctctc tttcggcatt taacgctaat gaagttcgtg gtgaacaact tggggattg    180
```

```
tgcaaaaagt tctcaaagaa acgaaagcca aaaaagattt tggccatagc caaggaccat    240
cttgtcgtta tgttgctgca aaacatgcaa aaaatattgc ttctgttacc tctattaatg    300
gtgaccatgg ttcagagatt gcagatttgg tacgacgtat tgtacgtaag gatagtgtgc    360
cagaatatat tgctgatgca gaagctattg gtactattat tctacatttt caggtcatcg    420
cagtccacaa gatgccgttg ctgcattgga agcattaaca acaaatgtaa cgttaaagta    480
cccacaaggg ttacctgcca ttcgtggtgg aggagaagtt gtaaatggcg tctactatta    540
ttcatttggt tatattcaag gtttgattgt tgggaaaggc aatctactgg atcctactca    600
tgcagcaatg cgtgtattaa gtgcattctt tacacaaaat ggtttggtag gtcgtacaag    660
tatgcggtta ggactgatag attatgcaga tcatctggat atggtaaatc aggttgctgg    720
gttagtaggg cgtggagata ttgttgctat ttatacaaac catgcgaatt ttttagcaag    780
aaagcttta                                                            789
```

<210> SEQ ID NO 13
<211> LENGTH: 263
<212> TYPE: PRT
<213> ORGANISM: Proteus sp.

<400> SEQUENCE: 13

```
Met Pro Thr Thr Tyr Pro Ile Val Leu Val His Gly Leu Ser Gly Phe
1               5                   10                  15

Asp Asn Val Val Gly Tyr Pro Tyr Phe Tyr Gly Ile Ala Asp Ala Leu
                20                  25                  30

Glu Lys Asp Gly His Lys Val Phe Thr Ala Ser Leu Ser Ala Phe Asn
            35                  40                  45

Ala Asn Glu Val Arg Gly Glu Gln Leu Trp Gly Leu Cys Lys Lys Phe
        50                  55                  60

Ser Lys Lys Arg Lys Pro Lys Lys Ile Leu Ala Ile Ala Lys Asp His
65                  70                  75                  80

Leu Val Val Met Leu Leu Gln Asn Met Gln Lys Ile Leu Leu Leu Leu
                85                  90                  95

Pro Leu Leu Met Val Thr Met Val Gln Arg Leu Gln Ile Trp Tyr Asp
            100                 105                 110

Val Leu Tyr Val Arg Ile Val Cys Gln Asn Ile Leu Leu Met Gln Lys
        115                 120                 125

Leu Leu Val Leu Leu Phe Tyr Ile Phe Arg Ser Ser Gln Ser Thr Arg
130                 135                 140

Cys Arg Cys Cys Ile Gly Ser Ile Asn Asn Lys Cys Asn Val Lys Val
145                 150                 155                 160

Pro Thr Arg Val Thr Cys His Ser Trp Trp Arg Arg Ser Cys Lys Trp
                165                 170                 175

Arg Leu Leu Leu Phe Ile Trp Leu Tyr Ser Arg Phe Asp Cys Trp Glu
            180                 185                 190

Arg Gln Ser Thr Gly Ser Tyr Ser Cys Ser Asn Ala Cys Ile Lys Cys
        195                 200                 205

Ile Leu Tyr Thr Lys Trp Phe Gly Arg Ser Tyr Lys Tyr Ala Val Arg
    210                 215                 220

Thr Asp Arg Leu Cys Arg Ser Ser Gly Tyr Gly Lys Ser Gly Cys Trp
225                 230                 235                 240

Val Ser Arg Ala Trp Arg Tyr Cys Cys Tyr Leu Tyr Lys Pro Cys Glu
                245                 250                 255
```

Phe Phe Ser Lys Lys Ala Leu
            260

<210> SEQ ID NO 14
<211> LENGTH: 942
<212> TYPE: DNA
<213> ORGANISM: Ocimum basilicum

<400> SEQUENCE: 14

| | | | | | |
|---|---|---|---|---|---|
| atggaggaaa | atgggatgaa | aagcaagatt | ttaatatttg | gagggacagg | ttacattgga | 60 |
| aatcacatgg | tgaaaggaag | cctcaaatta | gggcacccaa | cttatgtttt | cacaaggcct | 120 |
| aattcctcca | agacaaccct | tcttgatgag | ttccaatcct | tgggtgccat | catagtcaag | 180 |
| ggagagttgg | atgagcatga | gaaactagtt | gagttgatga | agaaagttga | tgttgtcata | 240 |
| tctgcacttg | cattcccaca | aattcttgat | cagttcaaga | tcttggaggc | catcaaggtt | 300 |
| gctgggaata | ttaagaggtt | tctaccgtcg | gattttgggg | tcgaggagga | cagaataaac | 360 |
| gcattgccgc | cgttcgaagc | actcatagag | aggaagagga | tgatcagaag | agccattgaa | 420 |
| gaagcaaata | ttccttacac | ttatgtgtct | gcaaattgct | ttgcatcata | cttcatcaac | 480 |
| tacttgctcc | gcccttatga | tccaaaagat | gagatcacgg | tttacggcac | cggggaagct | 540 |
| aagttcgcga | tgaactacga | caagacatc  | gggctctaca | cgatcaaagt | tgcaactgat | 600 |
| cctagagcat | tgaatcgtgt | ggtgatctac | agaccatcaa | caaatatcat | aacacagctc | 660 |
| gagttgattt | cgaggtggga | gaaaaaaatt | gggaagaagt | tcaaaaagat | tcatgtcccc | 720 |
| gaagaagaaa | ttgtggccct | cacaaaagaa | ctgccggagc | cgagaatat  | acccatagca | 780 |
| atccttcact | gtctcttcat | agacggagcg | acgatgagtt | atgatttcaa | ggagaacgat | 840 |
| gtggaggctt | caactctgta | tccagagttg | aagttcacca | cgatcgatga | gctcctcgac | 900 |
| attttcgtgc | acgatcctcc | accgccggct | tcagcagcat | tt | | 942 |

<210> SEQ ID NO 15
<211> LENGTH: 314
<212> TYPE: PRT
<213> ORGANISM: Ocimum basilicum

<400> SEQUENCE: 15

Met Glu Glu Asn Gly Met Lys Ser Lys Ile Leu Ile Phe Gly Gly Thr
1               5                   10                  15

Gly Tyr Ile Gly Asn His Met Val Lys Gly Ser Leu Lys Leu Gly His
            20                  25                  30

Pro Thr Tyr Val Phe Thr Arg Pro Asn Ser Ser Lys Thr Thr Leu Leu
        35                  40                  45

Asp Glu Phe Gln Ser Leu Gly Ala Ile Ile Val Lys Gly Glu Leu Asp
    50                  55                  60

Glu His Glu Lys Leu Val Glu Leu Met Lys Lys Val Asp Val Val Ile
65                  70                  75                  80

Ser Ala Leu Ala Phe Pro Gln Ile Leu Asp Gln Phe Lys Ile Leu Glu
                85                  90                  95

Ala Ile Lys Val Ala Gly Asn Ile Lys Arg Phe Leu Pro Ser Asp Phe
            100                 105                 110

Gly Val Glu Glu Asp Arg Ile Asn Ala Leu Pro Phe Glu Ala Leu
        115                 120                 125

Ile Glu Arg Lys Arg Met Ile Arg Arg Ala Ile Glu Glu Ala Asn Ile
    130                 135                 140

Pro Tyr Thr Tyr Val Ser Ala Asn Cys Phe Ala Ser Tyr Phe Ile Asn

```
                145                 150                 155                 160
Tyr Leu Leu Arg Pro Tyr Asp Pro Lys Asp Glu Ile Thr Val Tyr Gly
                165                 170                 175

Thr Gly Glu Ala Lys Phe Ala Met Asn Tyr Glu Gln Asp Ile Gly Leu
            180                 185                 190

Tyr Thr Ile Lys Val Ala Thr Asp Pro Arg Ala Leu Asn Arg Val Val
        195                 200                 205

Ile Tyr Arg Pro Ser Thr Asn Ile Ile Thr Gln Leu Glu Leu Ile Ser
    210                 215                 220

Arg Trp Glu Lys Lys Ile Gly Lys Lys Phe Lys Lys Ile His Val Pro
225                 230                 235                 240

Glu Glu Glu Ile Val Ala Leu Thr Lys Glu Leu Pro Glu Pro Glu Asn
                245                 250                 255

Ile Pro Ile Ala Ile Leu His Cys Leu Phe Ile Asp Gly Ala Thr Met
            260                 265                 270

Ser Tyr Asp Phe Lys Glu Asn Asp Val Glu Ala Ser Thr Leu Tyr Pro
        275                 280                 285

Glu Leu Lys Phe Thr Thr Ile Asp Glu Leu Leu Asp Ile Phe Val His
    290                 295                 300

Asp Pro Pro Pro Ala Ser Ala Ala Phe
305                 310

<210> SEQ ID NO 16
<211> LENGTH: 2577
<212> TYPE: DNA
<213> ORGANISM: Glycine max

<400> SEQUENCE: 16
atgacaggtg ggatgtttgg aaggaagggg caaaagataa aggggacagt ggtgttgatg      60
ccaaagaatg tgttggactt caacgccata acctccgtcg aaaaggcag tgctaaggac      120 accgccaccg atttcttggg caaaggcttg acgcattag gtcatgcagt tgatgctctc      180
actgccttcg ctggccatag catctccttg cagcttatca gtgctactca gactgatggt      240
agtggaaaag gaaagttgg aaacgaagcc tatttggaaa acatcttcc gaccttgcca      300 acgttgggag caaggcagga agcattcgat attaactttg aatgggatgc tagttttgga      360
attccaggag cattttacat caaaaacttt atgactgatg agttttttcct cgtcagtgtt      420 aaactcgagg acattccaaa ccatggaacc attaacttcg tttgtaactc atgggtttat      480
aacttcaaaa gttacaaaaa gaatcgcatt ttctttgtca atgatacata tcttccgagt      540
gctacaccag gtccactagt taagtacaga caagaagaat tggaggtttt aagaggagat      600
ggaacaggga agcgcagaga ctttgacaga atctatgatt atgatatcta taatgatttg      660
ggcaatccag atggtggtga tcctcgccca atcattggag gctctagcaa ctatccttac      720
cctcgcaggg ttagaaccgg tagaaaaag accaggaaag atcccaacag tgagaaacca      780
ggcgagatat atgttccaag agatgaaaac ttcggtcact gaagtcatc tgatttcctt      840 acatatggaa tcaaatcctt atctcagaac gtgataccttt tgttcaaatc tataatattg      900
aacttaaggg tcatcgagt gagttcgat agcttgacg aagtgcgtgg tctcttttgaa      960 ggtggaatca agctgccaac aaaatatactg agccaaatta gccccttacc agtcctcaag     1020
gaaatcttcc gcactgatgg tgaaaatacc cttcaatttc caccacctca tgtaatcaga     1080
gttagtaaat ctggatggat gactgatgat gagtttgcaa gagagatgat tgctggtgta     1140
aatccaaatg taattcgtcg tcttcaagag ttcccaccaa aaagcactct tgatcccgca     1200
```

-continued

```
acctatggtg atcaaactag taccataaca aaacaacagt tggagattaa cttgggtggg    1260
gtcacagtag aagaggcaat tagtgctcac agattattca tattagatta ccatgatgca    1320
ttcttcccgt atttgacgaa gataaacagc ctacctattg caaaagctta tgccacaagg    1380
acaatcctgt tcttgaaaga cgatggatct ttaaagccac ttgctatcga attaagcaag    1440
cctgcaacag tgagtaaagt ggtgttgcct gcaacagaag gtgttgagag tacaatttgg    1500
ttgttggcca aggctcatgt cattgtgaat gactctggtt atcatcagct cataagccat    1560
tggttaaata ctcatgcagt gatggagcca tttgccatag caacaaacag gcatctcagt    1620
gtgcttcacc ccatttataa acttctttat cctcactaca aggacacaat aaatatcaat    1680
ggccttgcta ggcagtccct gattaacgca ggtggcatta ttgagcaaac attttttgcct   1740
ggaaagtact ccattgaaat gtcatcagtt gtttacaaga atttgggtttt cactgaccaa    1800
gcattaccag ctgatcttgt caagagagga ttggcagttg aggatccctc tgccccacat    1860
ggtcttcgcc ttgtgataga ggactaccct tatgctgttg atggacttga aatatgggat    1920
gctattaaga catgggtcca tgagtatgtc tctgtgtatt acccaacaaa tgcagcaatt    1980
caacaagaca ctgaacttca agcatggtgg aaggaagttg tggagaaggg tcatggtgac    2040
ttaaaagata agccttggtg gcctaaactg cagactgtgg aggatctcat tcaatcctgc    2100
tctattatca tatggacagc ttcggctctc catgcagctg ttaattttgg caatacccct    2160
tatggaggtt atatcgtgaa ccgtccaact ctagccagaa ggtttatccc agaagaagga    2220
accaaagaat atgatgagat ggtgaaggat cctcaaaagg catatctgag aacaatcaca    2280
cccaagttcg agacccttat tgacatttca gtgatagaga tattgtcaag gcatgcttct    2340
gatgaggtct accttggcca aagggataat ccaaattgga ctacggattc aaaggcattg    2400
gaagctttca aaaagtttgg aaacaaactg gcagaaattg agggaaaaat cacacagagg    2460
aacaatgatc caagtctgaa aagccgacat gggccagttc agcttccata cacattgctc    2520
catcgttcaa gtgaggaagg gatgagtttc aaaggaattc ccaacagtat ctccatc      2577
```

<210> SEQ ID NO 17
<211> LENGTH: 859
<212> TYPE: PRT
<213> ORGANISM: Glycine max

<400> SEQUENCE: 17

```
Met Thr Gly Gly Met Phe Gly Arg Lys Gly Gln Lys Ile Lys Gly Thr
1               5                   10                  15
Val Val Leu Met Pro Lys Asn Val Leu Asp Phe Asn Ala Ile Thr Ser
            20                  25                  30
Val Gly Lys Gly Ser Ala Lys Asp Thr Ala Thr Asp Phe Leu Gly Lys
        35                  40                  45
Gly Leu Asp Ala Leu Gly His Ala Val Asp Ala Leu Thr Ala Phe Ala
    50                  55                  60
Gly His Ser Ile Ser Leu Gln Leu Ile Ser Ala Thr Gln Thr Asp Gly
65                  70                  75                  80
Ser Gly Lys Gly Lys Val Gly Asn Glu Ala Tyr Leu Glu Lys His Leu
                85                  90                  95
Pro Thr Leu Pro Thr Leu Gly Ala Arg Gln Glu Ala Phe Asp Ile Asn
            100                 105                 110
Phe Glu Trp Asp Ala Ser Phe Gly Ile Pro Gly Ala Pro Tyr Ile Lys
        115                 120                 125
```

```
Asn Phe Met Thr Asp Glu Phe Phe Leu Val Ser Val Lys Leu Glu Asp
    130                 135                 140

Ile Pro Asn His Gly Thr Ile Asn Phe Val Cys Asn Ser Trp Val Tyr
145                 150                 155                 160

Asn Phe Lys Ser Tyr Lys Lys Asn Arg Ile Phe Phe Val Asn Asp Thr
                165                 170                 175

Tyr Leu Pro Ser Ala Thr Pro Gly Pro Leu Val Lys Tyr Arg Gln Glu
            180                 185                 190

Glu Leu Glu Val Leu Arg Gly Asp Gly Thr Gly Lys Arg Arg Asp Phe
        195                 200                 205

Asp Arg Ile Tyr Asp Tyr Asp Ile Tyr Asn Asp Leu Gly Asn Pro Asp
210                 215                 220

Gly Gly Asp Pro Arg Pro Ile Ile Gly Gly Ser Ser Asn Tyr Pro Tyr
225                 230                 235                 240

Pro Arg Arg Val Arg Thr Gly Arg Glu Lys Thr Arg Lys Asp Pro Asn
                245                 250                 255

Ser Glu Lys Pro Gly Glu Ile Tyr Val Pro Arg Asp Glu Asn Phe Gly
            260                 265                 270

His Leu Lys Ser Ser Asp Phe Leu Thr Tyr Gly Ile Lys Ser Leu Ser
        275                 280                 285

Gln Asn Val Ile Pro Leu Phe Lys Ser Ile Ile Leu Asn Leu Arg Val
290                 295                 300

Thr Ser Ser Glu Phe Asp Ser Phe Asp Glu Val Arg Gly Leu Phe Glu
305                 310                 315                 320

Gly Gly Ile Lys Leu Pro Thr Asn Ile Leu Ser Gln Ile Ser Pro Leu
                325                 330                 335

Pro Val Leu Lys Glu Ile Phe Arg Thr Asp Gly Glu Asn Thr Leu Gln
            340                 345                 350

Phe Pro Pro Pro His Val Ile Arg Val Ser Lys Ser Gly Trp Met Thr
        355                 360                 365

Asp Asp Glu Phe Ala Arg Glu Met Ile Ala Gly Val Asn Pro Asn Val
370                 375                 380

Ile Arg Arg Leu Gln Glu Phe Pro Pro Lys Ser Thr Leu Asp Pro Ala
385                 390                 395                 400

Thr Tyr Gly Asp Gln Thr Ser Thr Ile Thr Lys Gln Gln Leu Glu Ile
                405                 410                 415

Asn Leu Gly Gly Val Thr Val Glu Glu Ala Ile Ser Ala His Arg Leu
            420                 425                 430

Phe Ile Leu Asp Tyr His Asp Ala Phe Phe Pro Tyr Leu Thr Lys Ile
        435                 440                 445

Asn Ser Leu Pro Ile Ala Lys Ala Tyr Ala Thr Arg Thr Ile Leu Phe
450                 455                 460

Leu Lys Asp Asp Gly Ser Leu Lys Pro Leu Ala Ile Glu Leu Ser Lys
465                 470                 475                 480

Pro Ala Thr Val Ser Lys Val Val Leu Pro Ala Thr Glu Gly Val Glu
                485                 490                 495

Ser Thr Ile Trp Leu Leu Ala Lys Ala His Val Ile Val Asn Asp Ser
            500                 505                 510

Gly Tyr His Gln Leu Ile Ser His Trp Leu Asn Thr His Ala Val Met
        515                 520                 525

Glu Pro Phe Ala Ile Ala Thr Asn Arg His Leu Ser Val Leu His Pro
530                 535                 540

Ile Tyr Lys Leu Leu Tyr Pro His Tyr Lys Asp Thr Ile Asn Ile Asn
```

```
                545                 550                 555                 560
            Gly Leu Ala Arg Gln Ser Leu Ile Asn Ala Gly Gly Ile Ile Glu Gln
                                565                 570                 575

Thr Phe Leu Pro Gly Lys Tyr Ser Ile Glu Met Ser Ser Val Val Tyr
                            580                 585                 590

Lys Asn Trp Val Phe Thr Asp Gln Ala Leu Pro Ala Asp Leu Val Lys
                        595                 600                 605

Arg Gly Leu Ala Val Glu Asp Pro Ser Ala Pro His Gly Leu Arg Leu
                    610                 615                 620

Val Ile Glu Asp Tyr Pro Tyr Ala Val Asp Gly Leu Glu Ile Trp Asp
            625                 630                 635                 640

Ala Ile Lys Thr Trp Val His Glu Tyr Val Ser Val Tyr Tyr Pro Thr
                                645                 650                 655

Asn Ala Ala Ile Gln Gln Asp Thr Glu Leu Gln Ala Trp Trp Lys Glu
                            660                 665                 670

Val Val Glu Lys Gly His Gly Asp Leu Lys Asp Lys Pro Trp Trp Pro
                        675                 680                 685

Lys Leu Gln Thr Val Glu Asp Leu Ile Gln Ser Cys Ser Ile Ile Ile
                    690                 695                 700

Trp Thr Ala Ser Ala Leu His Ala Ala Val Asn Phe Gly Gln Tyr Pro
            705                 710                 715                 720

Tyr Gly Gly Tyr Ile Val Asn Arg Pro Thr Leu Ala Arg Arg Phe Ile
                                725                 730                 735

Pro Glu Glu Gly Thr Lys Glu Tyr Asp Glu Met Val Lys Asp Pro Gln
                            740                 745                 750

Lys Ala Tyr Leu Arg Thr Ile Thr Pro Lys Phe Glu Thr Leu Ile Asp
                        755                 760                 765

Ile Ser Val Ile Glu Ile Leu Ser Arg His Ala Ser Asp Glu Val Tyr
                    770                 775                 780

Leu Gly Gln Arg Asp Asn Pro Asn Trp Thr Thr Asp Ser Lys Ala Leu
            785                 790                 795                 800

Glu Ala Phe Lys Lys Phe Gly Asn Lys Leu Ala Glu Ile Glu Gly Lys
                                805                 810                 815

Ile Thr Gln Arg Asn Asn Asp Pro Ser Leu Lys Ser Arg His Gly Pro
                            820                 825                 830

Val Gln Leu Pro Tyr Thr Leu Leu His Arg Ser Ser Glu Glu Gly Met
                        835                 840                 845

Ser Phe Lys Gly Ile Pro Asn Ser Ile Ser Ile
                    850                 855

<210> SEQ ID NO 18
<211> LENGTH: 2169
<212> TYPE: DNA
<213> ORGANISM: Armillariella tabescens

<400> SEQUENCE: 18
atggccacca caactgtcca ccgggagcga ttcctggcag ataagtctgc tcctttgtgt       60
ggtatggata ttagaaagtc atttgatcag ctcagctcta aggaaaagct ctacacgcat      120
tacgtgaccg aagcttcttg gcgggcgca agaatcatcc aggctcagtg gaccccgcag       180
gcgacagatc tatatgatct gttgatcctt acgttcagcg taaatggaaa gctcgccgac      240
ctgaatgccc ttaagacgtc gtcaggcctt tcagaggacg attgggaggc cttgatacag      300
tacacggtcc aggtattgag caatcttgtc aactacaaga cgttcggatt tacgaagatc      360
```

```
attccccgcg tcgacgcaga aaagtttgag tcagtggtca aagcctctag caacgcagac    420
cagggctcgg cactattcac caagttgaaa caacacatat atgcgctttc tcctgagtca    480
gcgctattca ttggcaaaag gaaggacggt cacgtatcaa attactatct tggtgaacct    540
gttggagatg ctgaggtcga tgctatccag aatgtcgctg agaagttagg cgttgatatc    600
ctcaatactc gcgtgaagaa gaatggagcg ggtgattaca cgctcttagt tgcctctgct    660
aaaaccagtc caccctccgt gcatgacttc caaatcgact caactccggc taaattgacg    720
attgagtatg cgactacgc gtcatctcta acgaaggttg tcgccgccct tcaggaggcc    780
aaacagtata ccgcgaacga tcatcaatca gcgatgatcg aaggctatgt caagtcgttc    840
aactcaggat caattccgga cacaaagct gcgtcaacag aatgggtgaa agatattgga    900
ccggttgtag agtcctacat cgggttcgtc gaaacctatg tcgacccata tggcggacgc    960
gcggaatggg agggttttcac tgccatcgtc gacaagcagc tgagtgcgaa gtacgaagca    1020
ttggttaacg tgctcctaa gttgatcaag agtcttccgt ggggaacgga cttcgaggtt    1080
gacgtcttca ggaagccgga ctttactgcg ttggaagtcg tatcatttgc aacaggaggt    1140
attcctgccg gaatcaatat accaaactat tatgaagtcc gggaaagcac agggtttaag    1200
aatgtttcgc tagcgaatat tttggcggcc aaggtaccaa acgaggagtt aactttcatc    1260
catcctgatg acgtagaact atataacgct tgggatagtc gcgcgtttga acttcaggtg    1320
gccaaccacg aacttttggg tcatggctcc ggcaagcttt tccaagaagg tgctgatggg    1380
aaactgaact tcgatcccga aaaggtcata aaccctctga ctggaaagcc gataacttca    1440
tggtataagc cagggcaaac gccggattct gttttaggcg aagtgtcgtc gtcaatggaa    1500
gaatgtcggg cggagaccgt agcgctctac ttggttagca acctcgatat tcttaaaatt    1560
ttcaattacg tcgacaagca agacattgaa gatatccagt acatcacgtt cttgcttatg    1620
gcccgcgctg gtctgcgggc actagagttt tatgatccag ccaccaagaa gcacggacag    1680
gcacatatgc aggccagaat gggcataacc cagtacctga ttcaagctgg gattgcgaga    1740
cttgaattga tccaggatgc caacggcgaa ctcgaaaact tatacgttcg ggttgaccgg    1800
gagaaagtgt tgtccaaagg aaaggaggtt gttggtcaat tgctgatcga actccaagtc    1860
cggaaaagta ccgcagacgg caccggctcc cgagatttct acacaacgct gaccgaacca    1920
atctctggat gggagggcaa gatccgagac atcgttttga agaagaagct tcctcgaaaa    1980
atctttgtcc aacccaatac atttgtcgtc aacggcgaag tccagctcaa agagtatcct    2040
ttgacggctg ccggggtaat tgaaagtttc attgagagac gattgtgtca gagccaattg    2100
acaaacattg atgaatgtag taaacgtgat cgtagcgata agatgtattc aaataacaat    2160
tctacccaa                                                            2169
```

<210> SEQ ID NO 19
<211> LENGTH: 723
<212> TYPE: PRT
<213> ORGANISM: Armillariella tabescens

<400> SEQUENCE: 19

Met Ala Thr Thr Thr Val His Arg Glu Arg Phe Leu Ala Asp Lys Ser
1               5                   10                  15

Ala Pro Leu Cys Gly Met Asp Ile Arg Lys Ser Phe Asp Gln Leu Ser
            20                  25                  30

Ser Lys Glu Lys Leu Tyr Thr His Tyr Val Thr Glu Ala Ser Trp Ala
        35                  40                  45

```
Gly Ala Arg Ile Ile Gln Ala Gln Trp Thr Pro Gln Ala Thr Asp Leu
     50                  55                  60

Tyr Asp Leu Leu Ile Leu Thr Phe Ser Val Asn Gly Lys Leu Ala Asp
 65                  70                  75                  80

Leu Asn Ala Leu Lys Thr Ser Ser Gly Leu Ser Glu Asp Asp Trp Glu
                 85                  90                  95

Ala Leu Ile Gln Tyr Thr Val Gln Val Leu Ser Asn Leu Val Asn Tyr
                100                 105                 110

Lys Thr Phe Gly Phe Thr Lys Ile Ile Pro Arg Val Asp Ala Glu Lys
            115                 120                 125

Phe Glu Ser Val Val Lys Ala Ser Ser Asn Ala Asp Gln Gly Ser Ala
    130                 135                 140

Leu Phe Thr Lys Leu Lys Gln His Ile Tyr Ala Leu Ser Pro Glu Ser
145                 150                 155                 160

Ala Leu Phe Ile Gly Lys Arg Lys Asp Gly His Val Ser Asn Tyr Tyr
                165                 170                 175

Leu Gly Glu Pro Val Gly Asp Ala Glu Val Asp Ala Ile Gln Asn Val
                180                 185                 190

Ala Glu Lys Leu Gly Val Asp Ile Leu Asn Thr Arg Val Lys Lys Asn
            195                 200                 205

Gly Ala Gly Asp Tyr Thr Leu Leu Val Ala Ser Ala Lys Thr Ser Pro
210                 215                 220

Pro Ser Val His Asp Phe Gln Ile Asp Ser Thr Pro Ala Lys Leu Thr
225                 230                 235                 240

Ile Glu Tyr Gly Asp Tyr Ala Ser Ser Leu Thr Lys Val Val Ala Ala
                245                 250                 255

Leu Gln Glu Ala Lys Gln Tyr Thr Ala Asn Asp His Gln Ser Ala Met
            260                 265                 270

Ile Glu Gly Tyr Val Lys Ser Phe Asn Ser Gly Ser Ile Pro Glu His
        275                 280                 285

Lys Ala Ala Ser Thr Glu Trp Val Lys Asp Ile Gly Pro Val Val Glu
    290                 295                 300

Ser Tyr Ile Gly Phe Val Glu Thr Tyr Val Asp Pro Tyr Gly Gly Arg
305                 310                 315                 320

Ala Glu Trp Glu Gly Phe Thr Ala Ile Val Asp Lys Gln Leu Ser Ala
                325                 330                 335

Lys Tyr Glu Ala Leu Val Asn Gly Ala Pro Lys Leu Ile Lys Ser Leu
            340                 345                 350

Pro Trp Gly Thr Asp Phe Glu Val Asp Val Phe Arg Lys Pro Asp Phe
        355                 360                 365

Thr Ala Leu Glu Val Val Ser Phe Ala Thr Gly Gly Ile Pro Ala Gly
    370                 375                 380

Ile Asn Ile Pro Asn Tyr Tyr Glu Val Arg Glu Ser Thr Gly Phe Lys
385                 390                 395                 400

Asn Val Ser Leu Ala Asn Ile Leu Ala Ala Lys Val Pro Asn Glu Glu
                405                 410                 415

Leu Thr Phe Ile His Pro Asp Val Glu Leu Tyr Asn Ala Trp Asp
            420                 425                 430

Ser Arg Ala Phe Glu Leu Gln Val Ala Asn His Glu Leu Leu Gly His
        435                 440                 445

Gly Ser Gly Lys Leu Phe Gln Glu Gly Ala Asp Gly Lys Leu Asn Phe
    450                 455                 460

Asp Pro Glu Lys Val Ile Asn Pro Leu Thr Gly Lys Pro Ile Thr Ser
```

```
              465                 470                 475                 480
        Trp Tyr Lys Pro Gly Gln Thr Pro Asp Ser Val Leu Gly Glu Val Ser
                        485                 490                 495

Ser Ser Met Glu Glu Cys Arg Ala Glu Thr Val Ala Leu Tyr Leu Val
                    500                 505                 510

Ser Asn Leu Asp Ile Leu Lys Ile Phe Asn Tyr Val Asp Lys Gln Asp
                515                 520                 525

Ile Glu Asp Ile Gln Tyr Ile Thr Phe Leu Leu Met Ala Arg Ala Gly
            530                 535                 540

Leu Arg Ala Leu Glu Phe Tyr Asp Pro Ala Thr Lys Lys His Gly Gln
        545                 550                 555                 560

Ala His Met Gln Ala Arg Met Gly Ile Thr Gln Tyr Leu Ile Gln Ala
                        565                 570                 575

Gly Ile Ala Arg Leu Glu Leu Ile Gln Asp Ala Asn Gly Glu Leu Glu
                    580                 585                 590

Asn Leu Tyr Val Arg Val Asp Arg Glu Lys Val Leu Ser Lys Gly Lys
                595                 600                 605

Glu Val Val Gly Gln Leu Leu Ile Glu Leu Gln Val Arg Lys Ser Thr
            610                 615                 620

Ala Asp Gly Thr Gly Ser Arg Asp Phe Tyr Thr Thr Leu Thr Glu Pro
        625                 630                 635                 640

Ile Ser Gly Trp Glu Gly Lys Ile Arg Asp Ile Val Leu Lys Lys Lys
                        645                 650                 655

Leu Pro Arg Lys Ile Phe Val Gln Pro Asn Thr Phe Val Asn Gly
                    660                 665                 670

Glu Val Gln Leu Lys Glu Tyr Pro Leu Thr Ala Ala Gly Val Ile Glu
                675                 680                 685

Ser Phe Ile Glu Arg Arg Leu Cys Gln Ser Gln Leu Thr Asn Ile Asp
            690                 695                 700

Glu Cys Ser Lys Arg Asp Arg Ser Asp Lys Met Tyr Ser Asn Asn
        705                 710                 715                 720

Ser Thr Gln

<210> SEQ ID NO 20
<211> LENGTH: 101
<212> TYPE: PRT
<213> ORGANISM: Homo sapiens

<400> SEQUENCE: 20

Asp Ala Asp Ala Glu Phe Arg His Asp Ser Gly Tyr Glu Val His His
  1               5                  10                  15

Gln Lys Leu Val Phe Phe Ala Glu Asp Val Gly Ser Asn Lys Gly Ala
            20                  25                  30

Ile Ile Gly Leu Met Val Gly Gly Val Val Ile Ala Thr Val Ile Val
        35                  40                  45

Ile Thr Leu Val Met Leu Lys Lys Lys Gln Tyr Thr Ser Ile His His
    50                  55                  60

Gly Val Val Glu Val Asp Ala Ala Val Thr Pro Glu Glu Arg His Leu
65                  70                  75                  80

Ser Lys Met Gln Gln Asn Gly Tyr Glu Asn Pro Thr Tyr Lys Phe Phe
                85                  90                  95

Glu Gln Met Gln Asn
            100
```

```
<210> SEQ ID NO 21
<211> LENGTH: 10
<212> TYPE: PRT
<213> ORGANISM: Homo sapiens

<400> SEQUENCE: 21

Leu Lys Pro Tyr Gly Ala Leu Val Asp Lys
1               5                   10

<210> SEQ ID NO 22
<211> LENGTH: 7
<212> TYPE: PRT
<213> ORGANISM: Homo sapiesn

<400> SEQUENCE: 22

Met Cys Ser Cys Cys Glu Lys
1               5

<210> SEQ ID NO 23
<211> LENGTH: 9
<212> TYPE: PRT
<213> ORGANISM: Homo sapiens

<400> SEQUENCE: 23

Gly Val Phe His Gln Thr Val Ser Arg
1               5

<210> SEQ ID NO 24
<211> LENGTH: 16
<212> TYPE: PRT
<213> ORGANISM: Homo sapiens

<400> SEQUENCE: 24

Arg Gln Ile Lys Ile Asn Phe Gln Asn Arg Arg Met Lys Trp Lys Lys
1               5                   10                  15

<210> SEQ ID NO 25
<211> LENGTH: 15
<212> TYPE: PRT
<213> ORGANISM: Homo sapiens

<400> SEQUENCE: 25

Arg Val Arg Val Trp Phe Gln Asn Lys Arg Cys Lys Asp Lys Lys
1               5                   10                  15
```

VECTOR CONTAINING MULTIPLE NUCLEOTIDE SEQUENCES FOR THE EXPRESSION OF ENZYMES

CROSS REFERENCE TO RELATED APPLICATIONS

This application claims the priority benefit of the U.S. Provisional Patent Application Ser. No. 61/826,545 filed on May 23, 2013, the entire contents of which are hereby incorporated by reference.

FIELD OF INVENTION

This invention relates to recombinant DNA in general and, more particularly, to recombinant DNA containing specific nucleotide sequences for the expression of peptides and proteins, and methods of using the recombinant DNA to produce the peptides and proteins.

SEQUENCE LISTING

This application contains a Sequence Listing which has been submitted in ASCII format via EFS-Web and is hereby incorporated by reference in its entirety. The ASCII copy, created on May 23, 2014, is named sequence.txt and is 45,056 bytes in size.

A paper copy of the Sequence Listing has been submitted in PDF format via EFS-Web and is hereby incorporated by reference in its entirety. Applicants hereby state that the information recorded in computer readable form is identical to the written sequence listing.

BACKGROUND

An important goal of recombinant DNA technology is to obtain efficient expression of the cloned DNA. The cloning vector, widely used in molecular biology, is a small piece of DNA molecule, in which a foreign DNA fragment may be inserted. The cloning vector may be used as vehicle to transfer foreign genetic material into a cell. Insertion of the foreign DNA fragment into the cloning vector is usually carried out by (1) digesting both the vector and the foreign DNA with restriction enzyme; and (2) ligating the restriction enzyme digested fragments together. Vectors can be used for controlled expression of particular genes, with promoter sequence to drive transcription of the transgene cloned in the vector.

Once the vector is inside the cell, the protein that is encoded by the transgene is produced by cellular transcription and translation. After the expression of the gene product, the resulted protein of interest needs to be purified and isolated from other proteins of the host cell. To facilitate the purification and/or isolation process, the cloned transgene usually has a tag, such as histidine (His) tag. In addition, GFP (green fluorescent protein) sequence is often used as biomarker to follow the expression process. In cells where the tagged transgene is expressed, the GFP is also produced, and those cells can be observed under fluorescence microscopy and isolated by FACS.

Enzymes are proteins that catalyze chemical reactions. Almost all processes in biological cells need enzymes. Enzymes are widely used in the chemical industry and other industrial applications. For example, enzymes can be applied in the fermentation industry as food additives, and are also commonly used in food processing and in the production of food ingredients. Traditionally, enzymes are isolated from cultivable microorganisms such as *E. coli.*, or plants, and mammalian tissues, and are often not well-adapted to the modern food production. The use of recombinant DNA (rDNA) and vector technology has made it possible to manufacture novel enzymes suitable for specific food-processing conditions. It is an urgent need in the field of application of biological enzymatic products for replacing any of the current potential harmful organic or synthesized chemical compounds for our public health.

For example, commonly used food sweeteners such as glucose or fructose syrups are typically produced from corn-starch using hydrolytic enzymes. In the first step of starch hydrolysis, starch is liquefied with α-amylase by heating at 105° C. for 2-5 min followed by 1-2 h at 90-100° C. With the advance of rDNA technology, it became possible to engineer amylases with increased heat stability and improved compatibility with other parameters of the liquefaction process. These improvements were accomplished by introducing changes in the α-amylase amino acid sequences through DNA sequence modifications of the α-amylase genes. Other enzymes currently used in food processing have also been improved using rDNA techniques.

The enzymes suitable for industrial application or other applications may be discovered by screening microorganisms sampled from diverse environments or developed by modification of known enzymes using modern methods of protein engineering or molecular evolution. As a result, several important food-processing enzymes such as amylases and lipases with properties tailored to particular food applications have become available (Table 1).

Enzymes produced by this vector system are also very useful in the fragrance/perfume industry. Chemical reagents have been used to produce scent compound to generate perfume with similar scent as those in nature counterparts. However, using chemical catalysis to produce active ingredients often produce both active form and its inactive twin form of molecules, as well as chemical reagents may remain as contamination in the final products. Enzyme is good to make only one of the versions to increase the purity of the final product without chemical toxicity. The enzyme used in the process is natural and scent produced is an exact replica of what is found in nature (i.e., in plant or animal); it thus can be considered as natural and health (perfume) products

TABLE 1

Enzymes from recombinant microorganisms (based on FDA regulations, GRAS affirmation petitions, and GRAS notices)

| Source microorganism | Enzymes | Reference* |
|---|---|---|
| *Aspergillus niger* | Phytase | GRASP 2G0381 |
| | Chymosin | 21 CFR 184.1685 |
| | Lipase | GRN 158 |
| *Aspergillus oxyzae* | Esterase-lipase | GRASP 7G0323 |
| | Aspartic proteinase | GRN 34 |
| | Glucose oxidase | GRN 106 |
| | Laccase | GRN 122 |
| | Lipase | GRN 43; GRN 75; GRN 103 |
| | Pectin esterase | GRN 8 |
| | Phospholipase A1 | GRN 142 |
| *Bacillus licheniformis* | α-amylase | GRASP 0G0363; GRN 22; GRN 24; GRN 79 |
| | Pullulanase | GRN 72 |
| *Bacillus subtilis* | α-acetolactate decarboxylase | 21 CFR 173.115 |
| | α-amylase | GRASP 4G0293; GRASP 7G0328 |

TABLE 1-continued

Enzymes from recombinant microorganisms (based on FDA regulations, GRAS affirmation petitions, and GRAS notices)

| Source microorganism | Enzymes | Reference* |
|---|---|---|
| | Maltogenic amylase | GRASP 7G0326 |
| | Pullulanase | GRN 20 |
| Escherichia coli K-12 | Chymosin | 21 CFR 184.1685 |
| Fusarium venenatum | Xylanase | GRN 54 |
| Kluyveromyces marxianus var. lactis | Chymosin | 21 CFR 184.1685 |
| Pseudomonas fluorescens Biovar 1 | α-amylase | GRN 126 |
| Trichoderma reesei | Pectin lyase | GRN 32 |

Reference: Z. S. Olempska-Beer et al./Regulatory Toxicology and Pharmacology 45 (2006) 144-158

In addition, there's need for using vector expression system as an economic biological method for large-scale production of cosmetic proteins or enzymes such as collagen, lipase, or other proteins or peptides, which are ideal candidates in whitening, depigmenting and wound-repairing applications. For example, novel engineered collagens with optimized biochemical and physical properties can be produced using either mammalian cell-lines or transgenic animals (Table 2).

TABLE 2

Comparison of the various recombinant expression systems for the production of collagen

| Expression host | Protein expressed | Yield (µg/ml) | Advantages | Disadvantages |
|---|---|---|---|---|
| Yeast (Pichia pastoris) | proα1(III) + α- and β-subunits of P4H | >15 | High yield, inexpensive | Not secreted, low hydroxylysine content |
| Insect cells | proα1(III) + α- and β-subunits of P4H | 60 | High yield | Not secreted |
| HT1080 | proα1(II), proα1(I), proα1(III) | 035-2 | Secreted, authentic product, no need for co-expression of P4H | Low yields |
| HEK 293-EBNA | proα1(V) | 15 | High yields, secreted, authentic product, no need for co-expression of P4H | Some cleavage of propeptides |
| Transgenic animals | Modified procollagens + α- and β-subunits of P4H | 150 | High yield, authentic product | High development costs |

Reference: Biochemical Society Transactions (2000) Volume 28, part 4

In the future, these recombinant proteins can be used both to investigate the molecular basis and biochemistry of collagen assembly and to produce collagens with new pharmaceutical and medical uses. Similarly, the vector expression system can be utilized to generate other gene-modified functional proteins, which have extensive application in skin repairing, healing and aging protection.

Vector expression system can also be used in stem cell and gene therapy. For example, Gaucher disease is a lysosomal storage disorder resulting from a deficiency of an enzyme, glucocerebrosidase (GC). Recently, lentivirus vectors have been developed for efficient gene transfer into hematopoietic stem cells (HSCs). A recombinant lentivirus vector was used to evaluate the transduction of the human GC gene into murine bone-marrow-derived HSCs and its expression in their progeny. The recombinant lentiviral vector transduces HSCs that are capable of long-term gene expression in vivo; which was described in US Patent Publication US20030119770A1. In addition, expression or production of fusion protein or enzyme, such as TatNP22-GC with capability to cross the blood brain-barrier is designed and made by the vector system. This approach is potentially useful for the treatment of patients with Gaucher disease, CNS disorders and other diseases.

Another application is recent development of lentiviral vector. It is especially useful for studies on gene or genomic function because the lentiviral vector can be used to achieve efficient integration of transgene into nondividing cell genomes and successful long-term expression of the transgene. These attributes make the vector useful for gene delivery, mutagenesis, and other applications in mammalian systems. This technique should facilitate the rapid enrichment and cloning of the trapped cells and provides an opportunity to select subpopulations of trapped cells based on the subcellular localization of reporter genes. Our findings suggest that the reporter gene is driven by an upstream, cell-specific promoter during cell culture and cell differentiation, which further supports the usefulness of lentivirus-based gene-trap vectors. Lentiviral gene-trap vectors appear to offer a wealth of possibilities for the study of cell differentiation and lineage commitment, as well as for the discovery of new genes, tacking the migration of gene products, and identifying markers for early-stage human cancer cells' progressing activity.

Implantation of the serotonergic-like progenitors into the hippocampus of adult mice genetically lacking SERT was followed by migration of these cells into adjacent brain regions, and survival of the cells for many months was accompanied by a gradual increase in density of SERT protein expression, which was not found in vehicle-injected, control mice. These findings suggest that this serotonergic-like NSC model will be a useful contribution to the development of cell biotechnology in regard to the expression of missing genes such as SERT in the adult brain by employing appropriate vectors.

BRIEF SUMMARY OF THE DISCLOSURE

One aspect of the present disclosure provides an expression vector for amplified expression of a transgene in a cell. The vector includes a promoter configured to drive the expression of the transgene in the cell. The vector also includes a tag sequence encoding a tag peptide directing the protein of the expressed transgene to a pre-determined location. The vector further includes a first cleavage sequence encoding a peptide that is recognizable by a protease and a marker gene configured to encoding a protein to indicate the expression of the transgene.

One objective of the present invention is to provide a DNA expression vector comprising a CMV (cytomegalovirus) promoter or mammalian cell promoters, inserted transgene, enzyme cleavage sites and GFP (green fluorescent protein) gene.

Another objective of the present invention is to provide a DNA expression vector comprises T7 promoter or CAG promoter, or bacterial or inset cells or yeast cells promoter, His-Tag, Thro-cleavage site, and inserted transgene.

Another objective of the invention is to provide a new method for preparing, by genetic engineering techniques, proteins including biologically active enzymes.

In one embodiment of the invention, transgene is a gene with the sequence substantially identical to a sequence selected from the group consisting of the SEQ ID No: 10, SEQ ID No: 12, SEQ ID No: 14, SEQ ID No: 16, and SEQ ID No: 18.

In the present disclosure, the procedure of preparing the expression vector is described.

In another embodiment of the invention, a genetically engineered transgene is inserted into the expression vector. Such engineered transgene may have high potent activity under different conditions such as high or lower temperature, in both in vitro and in vivo system.

Cellular and intercellular cleavage (CIC) sites or their derived sequence or mutated sequence with similar function of CIC are constructed in the vector for purification, screening or targeting purposes.

Different enzyme products may be produced using the expression vector as disclosed. The enzymes may be present together with their substrates in applications. For example, certain enzyme and substrates mixture formulation may be added into flour for baking industry. Such mixture may include components use for nutrition or antioxidant purpose.

DETAILED DESCRIPTION

The Reference will now be made in detail to exemplary embodiments of the invention, which are illustrated in the accompanying drawings. Wherever possible, the same reference numbers will be used throughout the drawings to refer to the same or like parts.

Figure 1:
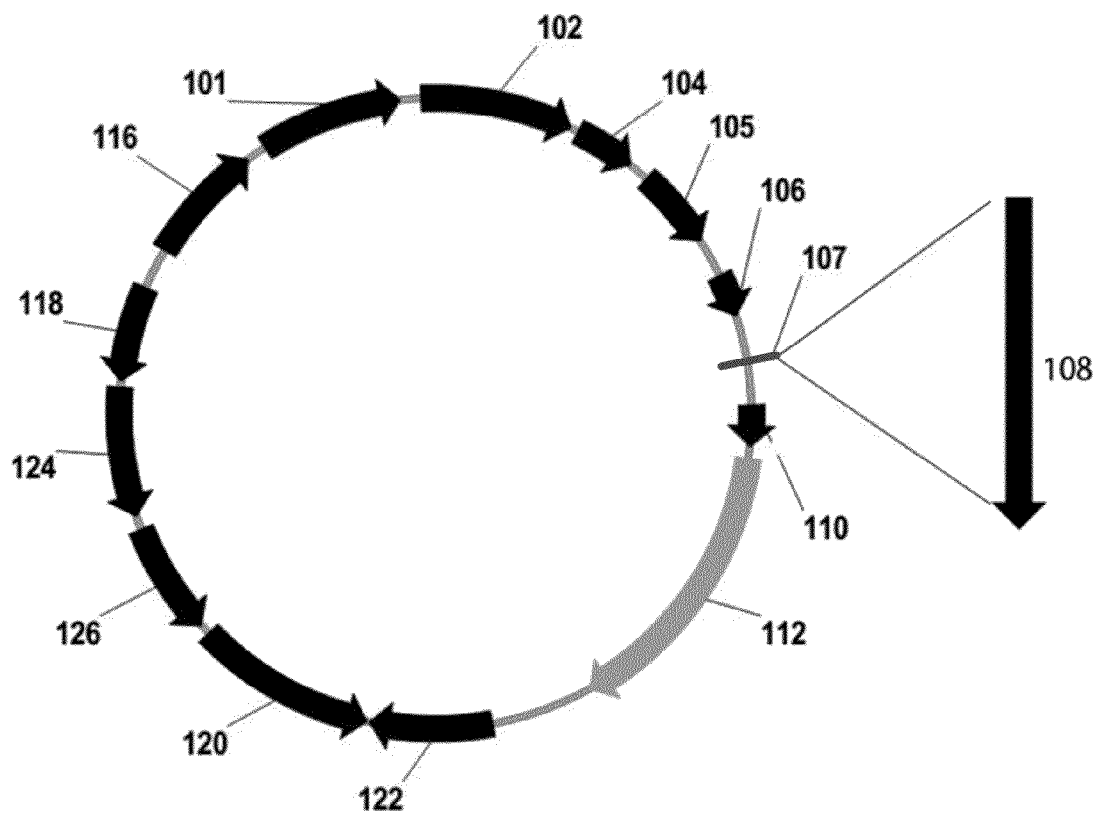
FIG. 1 illustrates an exemplary expression vector consistent with the disclosed embodiments.

FIG. 1 illustrates an exemplary vector 100 consistent with the disclosed embodiments. As shown in FIG. 1, the vector 100 may include a promoter 102, which may drive the expression of a gene in a mammalian cell. In certain embodiments, the promoter 102 may be a promoter as listed in Table 3, such as Cytomegalovirus (CMV) promoter. Other types of mammalian promoters may also be used. The promoter 102 may be derived from an organism, such as an animal, a plant, a bacterium, a eukaryotic microorganism, or a virus. The promoter 102 may also include one or more mutations to a sequence derived from an organism. The promoter 102 may also be artificially designed and/or synthesized.

TABLE 3

Promoters in Mammalian Cell Expression Vector

CMV: Cytomegalovirus Promoter
EF-1: Elongation Factor 1 Promoter
SYN1 (neuron specific-): Synapsin 1 Promoter
SP-B (lung cell specific): Surfactant Protein B Promoter
Survivin (tumor) Survivin Promoter
CD45(stem cell): CD 45 Promoter The vector 100 may include a sequence 104 encoding a signal peptide. The sequence 104 may be derived from an organism, such as an animal, a plant, a bacterium, a eukaryotic microorganism, or a virus. The sequence 104 may also include one or more mutations to a sequence derived from an organism. The sequence 104 may also be artificially designed and/or synthesized.

The vector 100 may also include a tag sequence 105. In certain embodiments, the sequence 105 may encode a target delivery peptide that may direct the expressed protein to certain location, for example, nucleus, peroxisome, certain specific type of cells, extracellular matrix, or outside of the cell. The targeting delivery peptide encoded by the sequence 105 may direct the expressed protein to any appropriate locations. Table 4 lists some exemplary target delivery peptides. One or more mutations may be introduced to the target delivery peptides listed in Table 4 such that the delivery ability of the peptide may be modified. The sequence 105 may encode a peptide with a sequence that is substantially identical to a sequence selected from the group consisting of SEQ ID No: 1, SEQ ID No: 2, SEQ ID No: 3, SEQ ID No: 24, and SEQ ID No: 25

In certain embodiments, the tag 105 may encode a peptide with a sequence having a sequence identity greater than eighty percent (80%), eighty five percent (85%), ninety percent (90%), ninety five percent (95%), or ninety nine percent (99%) to a sequence selected from the group consisting of SEQ ID No: 1, SEQ ID No: 2, SEQ ID No: 3, SEQ ID No: 24, and SEQ ID No: 25.

The tag 105 may encode a target delivery peptide derived from an organism, such as an animal, a plant, a bacterium, a eukaryotic microorganism, or a virus. The tag 105 may also encode a target delivery peptide that may include one or more mutations to a target delivery peptide derived from an organism. The tag 105 may also encode a target delivery peptide that is artificially designed and/or synthesized. The tag 105 may encode a peptide for any other appropriate purpose. The tag 105 may also encode two or more different type of peptide.

TABLE 4

| Source protein of the tag peptide | Sequence ID | Peptide sequence |
|---|---|---|
| AntpPTD | SEQ ID No: 1 | RQIKIWFQNRR |
| Hoxa-5PTD | SEQ ID No: 24 | RQIKINFQNRRMKWKK |
| Ist-1PTD | SEQ ID No: 25 | RVRVWFQNKRCKDKK |
| HIV-Tat | SEQ ID No: 2 | YGRKKRRQRRR |

TABLE 4-continued

| Source protein of the tag peptide | Sequence ID | Peptide sequence |
|---|---|---|
| VP-22 | SEQ ID No: 3 | MTSRRSVKSGPREVPR DEYEDLYYTPSSCMAS PDSPPDTSRRGALQTR ARPRGEVRFVQYDESD YALYGGSSSEDDEHPE VPRTRRPVSGAVLSAP GPARAPPPPAGSGGAG RTPTTAPRAPRTQRVA TKAPAAPAAETTRGRK SAQPESAALPDAPAST APTRSKTPAQGLARKL HFSTAPPNPDAPWTPR VAGFNKRVFCAAVGRL AAMHARMAAVQLWDMS RPRTDEDLNELLGITT IRVTVCEGKNLIQRAN ELVNPDVVQDVDAATA TRGRSAASRPTERPRA PARSASRPRRPV |

The vector 100 may further include a first cleavage site 106. The first cleavage site 106 may encode a peptide that may be specifically recognized by a protease. After the expression of the transgene, the tag peptide may be removed from the target protein by protease digestion. Table 5 lists some exemplary peptides encoded by the cleavage site 106. One or more mutations may be introduced to the peptides listed in Table 5 such that the efficiency of the protease digestion on the peptide may be modified. Thus, the cleavage site 106 may encode a peptide with a sequence that is substantially identical to one of the sequences listed in Table 5. The cleavage site 106 may encode a peptide with a sequence that is substantially identical to a sequence selected from the group consisting of SEQ ID No: 4, SEQ ID No: 5, SEQ ID No: 6, SEQ ID No: 7, SEQ ID No: 8, SEQ ID No: 20, SEQ ID No: 21, SEQ ID No: 22, and SEQ ID No: 23.

In certain embodiments, the site 106 may encode a peptide with a sequence having a sequence identity greater than eighty percent (80%), eighty five percent (85%), ninety percent (90%), ninety five percent (95%), or ninety nine percent (99%) identity to a sequence selected from the group consisting of SEQ ID No: 4, SEQ ID No: 5, SEQ ID No: 6, SEQ ID No: 7, SEQ ID No: 8, SEQ ID No: 20, SEQ ID No: 21, SEQ ID No: 22, and SEQ ID No: 23. The site 106 may encode a peptide that is recognized by a protease that recognizes a peptide with a sequence selected from the group consisting of SEQ ID No: 4, SEQ ID No: 5, SEQ ID No: 6, SEQ ID No: 7, SEQ ID No: 8, SEQ ID No: 20, SEQ ID No: 21, SEQ ID No: 22, and SEQ ID No: 23. The protease is also capable of cleave the peptide encoded by the site 106.

The cleavage site 106 may encode any other appropriate protease recognizable peptides. The cleavage site 106 may encode a peptide, which is recognizable by a protease, derived from an organism, such as an animal, a plant, a bacterium, a eukaryotic microorganism, or a virus. The cleavage site 106 may also encode a peptide that may include one or more mutations to a target delivery peptide derived from an organism. The cleavage site 106 may also encode a peptide target delivery peptide that is artificially designed and/or synthesized.

TABLE 5

| Source of Peptide | Sequence ID | Sequence |
|---|---|---|
| Furin 2A | SEQ ID No: 4 | LLNFDLLKLLAGDVESNPCP |
| Globin, Preprolactin | SEQ ID No: 5 | MDSKGSSQKGSRLLLLLVVSNLL LCQCVVSTPVCPNGPGNCQVSLR DLFDRAVMVSHYIHDLSSEMFNE FDKRYAQGKGFITMALNSCHT |
| Caspase-3, Caspase-8 | SEQ ID No: 6 | HHSDESDELVTDFPTDLPATEVFT PVVPTVDTYDGRGDSVVYG |
| Thrombin | SEQ ID No: 7 | CSIPVCGQDQVTVAMTPRSEGSSV NLSPPLEQCVPDRGQQY |
| Gamma-secretase | SEQ ID No: 20 | DADAEFRHDSGYEVHHQKLVFFA EDVGSNKGAIIGLMVGGVVIATVI VITLVMLKKKQYTSIHHGVVEVD AAVTPEERHLSKMQQNGYENPTY KFFEQMQN |
| USVG cleavage site (synthesized) | SEQ ID No: 8 / SEQ ID No: 9 | QTLNFDLLKLAGDVESNPGPGNS CAG ACT TTG AAT TTT GAC CTT CTC AAG TTG GCG GGA GAC GTC GAG TCC AAC CCT GGG CCC GGG AAT TCT- |
| MMP9 Cleavage site 1 | SEQ ID No: 21 | LKPYGALVDK |
| MMP9 Cleavage site 2 | SEQ ID No: 22 | MCSCCEK |
| MMP9 Cleavage site 3 | SEQ ID No: 23 | GVFHQTVSR |

The vector 100 may also include a multiple cloning site (MCS) 107. The MCS 107 may include a sequence that contains one or more restriction enzyme recognizing site. For example, the MCS 107 may include the restriction enzyme site for EcoRI, BamHI, NsiI, NdeI, HindIII, and other restriction enzymes. A transgene 108 may be introduced into the vector 100 through molecular cloning technique. For example, the transgene 108 may be digested by a first restriction enzyme and a second restriction enzyme. The vector 100 may be digested by the same first restriction enzyme and the second restriction enzyme. The digested transgene 108 and vector 100 may be ligated by a ligase.

The sequence 104, the tag sequence 105 and the first cleavage site 106 may be a part of the vector 100. The sequence 104, the tag sequence 105 and the first cleavage site 106 may also synthesized and linked to the transgene 108. A DNA molecule including the sequence 104, the tag sequence 105, the first cleavage site 106 and the transgene 108 may thus be introduced into the vector 100 downstream to the promoter 102.

The vector 100 may further include a second cleavage site 110. The second cleavage site 110 may be similar to the first cleavage site 106. After the expression of the recombinant gene, a protease digestion may remove other peptide that is attached to the target protein at its C-terminus. The second cleavage site 110 may be the same to the first cleavage site 106. That is, the cleavage sites 106 and 110 may have identical sequence. The second cleavage site 110 may also be different to the first cleavage site 106. That is, the cleavage sites 106 and 110 may have different sequence.

The vector 100 may also include a marker gene 112. The marker gene 112 may encode a fluorescent protein such as green fluorescent protein (GFP) or its variant, such as eukaryotic green fluorescent protein (EGFP), red fluorescent protein (RFP), or other fluorescent protein. The marker gene 112 may also encode any mutant fluorescent protein. The marker gene 112 may also encode any other protein that may be appropriate as a marker protein. In certain embodiments, the marker gene may encode a Cluster of Differentiation (CD) protein, such as CD25.

The marker gene 112 may encode a protein derived from an organism, such as an animal, a plant, a bacterium, a eukaryotic microorganism, or a virus. The marker gene 112 may also encode a protein that may include one or more mutations to a protein derived from an organism. The marker gene 112 may also encode a protein that is artificially designed and/or synthesized.

The vector 100 may also include an expression regulating sequence 101. The expression regulating sequence 101 may enhance or suppress the expression of the recombinant transgene 108. The expression regulating sequence 101 may also direct the expression of the recombinant transgene 108 in a temporal or spatial specific manner. For example, the expression regulating sequence 101 may be responsive to certain compound, such as IPTG, and induce the expression of the recombinant gene upon the addition of IPTG in cell culture. The expression regulating sequence 101 may also be responsive to developmental signal in vivo and/or in vitro.

The expression regulating sequence 101 may be located at an appropriate site as determined empirically. For example, the sequence 101 may be located to the 5' terminus of the promoter. The sequence 101 may also be located to the 3' terminus of the insert transgene 108. The sequence 101 may be derived from an organism, such as an animal, a plant, a bacterium, a eukaryotic microorganism, or a virus. The sequence 101 may also include one or more mutations to a sequence derived from an organism. The sequence 101 may also be artificially designed and/or synthesized.

The vector 100 may further include a first genomic integrating sequence 116. The genomic integrating sequence 116 may facilitate the integration of the recombinant DNA into a chromosome of a mammalian cell. The integrated recombinant DNA may include the expression regulating sequence 101, the promoter 102, the target delivery sequence 105, the first cleavage site 106, the transagene 108, the second cleavage site 110, and the marker gene 112. In certain embodiments, the vector 100 may includes a second integrating sequence 122, with each integrating sequence located at one end of the DNA to be integrated. The integrating sequences 116 and 122 may be a long terminal repeat (LTR) from a RNA virus, such as HIV. The integrating sequence may also be an inverted terminal repeat (ITR) from a DNA virus, such as adeno-associated virus (AAV).

The sequences 116 and 122 may be derived from an organism, such as an animal, a plant, a bacterium, a eukaryotic microorganism, or a virus. The sequences 116 and 122 may also include one or more mutations to a sequence derived from an organism. The sequence 116 and 122 may also be artificially designed and/or synthesized.

A cell may be transfected with a recombinant vector that include the inserted target gene in the vector 100. The target gene 108 may be transiently expressed in the cell. The target gene 108 may also be integrated into the genome of the cell. A cell line that includes the target gene may be established and may express the target gene.

The vector 100 may further include a first replication origin 126, a first selective marker 120, a second replication origin 118, and a second selective marker 124. In certain embodiments, the first replication origin 126 may be configured to enable the vector to be replicated in mammalian cells. In certain embodiments, the origin 126 may be a SV40 replication origin. Other mammalian replication origin may also be used. The first selective marker 120 may be configured to enable the selection of mammalian cells that contains the introduced vector. In certain embodiments, the selective marker 120 may be a neomycin resistant gene. Other selective marker may also be used.

In certain embodiments, the second replication origin 118 may enable the vector to replicate in a bacterium. In certain embodiments, the origin 118 may be a ColE1 origin. Other bacterial replication origin may also be used. The selective marker 124 may be an ampicillin resistance gene. Other selective marker may also be used.

Figure 2:
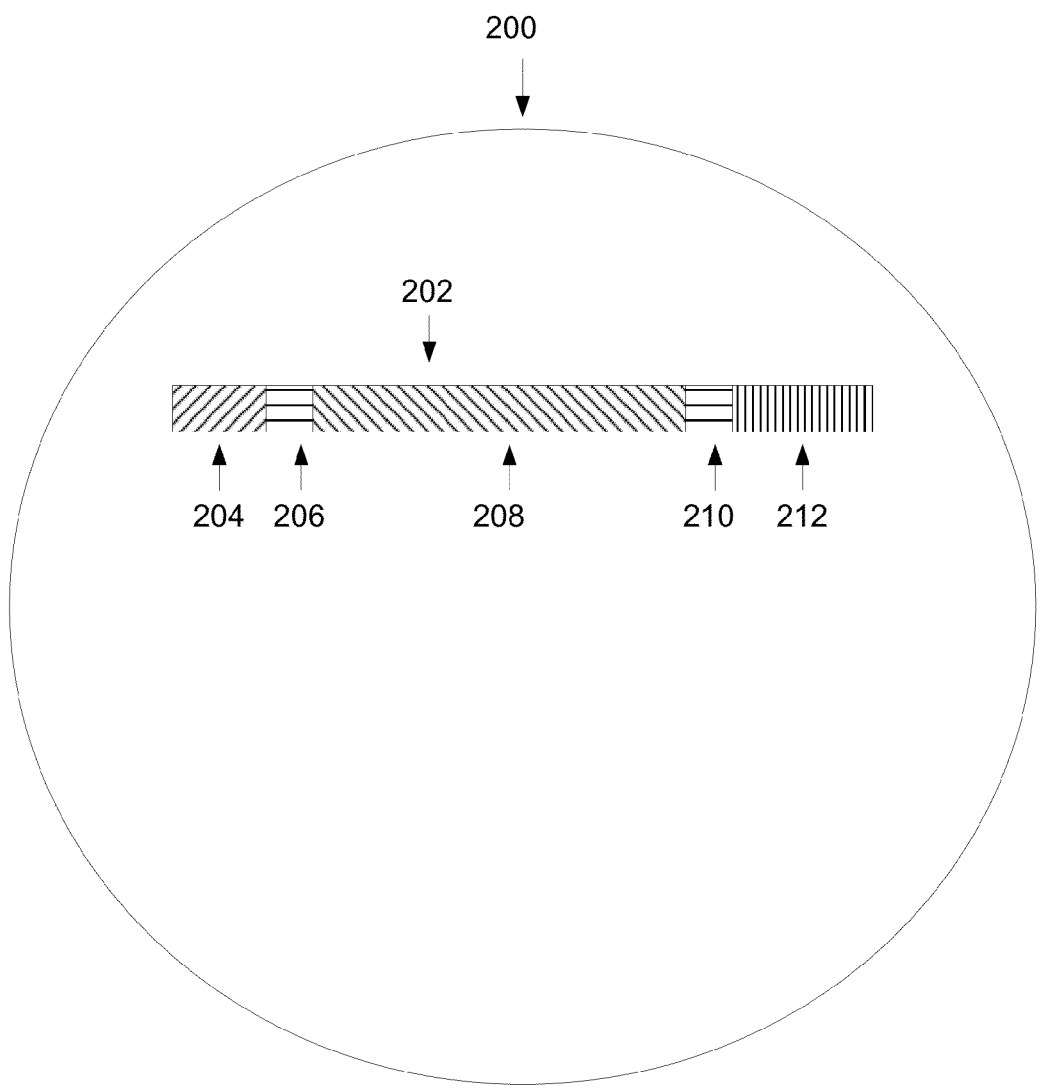
FIG. 2 illustrates an exemplary pre-activated protein expression consistent with the disclosed embodiments.

FIG. 2 illustrates an exemplary pre-activated protein 202 consistent with the disclosed embodiments. As shown in FIG. 2, a recombinant protein 202 may be generated in the cell 200. The recombinant protein 202 may include a target delivery peptide 204, a first cleavage peptide 206, a protein or peptide 208, a second cleavage peptide 210, and a marker protein 212. At this stage, the protein 208, which may have desired biological activity, may not exhibit any biological activity. In certain embodiments, the target delivery peptide 204 may be a HIV-Tat peptide, which may direct the recombinant protein 202 to certain target cells. In certain embodiments, the target delivery peptide 204 may have a sequence substantially identical to a sequence selected from the group consisting of the SEQ ID No: 1, SEQ ID No: 2, SEQ ID No: 3, SEQ ID No: 24, and SEQ ID No: 25. In certain embodiments, the target delivery peptide 204 may have a sequence with greater than eighty percent (80%), eighty five percent (85%), ninety percent (90%), ninety five percent (95%), or ninety nine percent (99%) identity to a sequence selected from the group consisting of the SEQ ID No: 1, SEQ ID No: 2, SEQ ID No: 3, SEQ ID No: 24, and SEQ ID No: 25. Other target delivery peptide 204 may be used to direct the recombinant protein 202 to certain locations.

The cleavage peptide 206 and 210 may be recognized by a protease and the protease may cleave the peptide 206 and 210. In certain embodiments, the cleavage peptide 206 or 210 may have a sequence substantially identical to a sequence selected from the group consisting of the SEQ ID No: 4, SEQ ID No: 5, SEQ ID No: 6, SEQ ID No: 7, SEQ ID No: 8, SEQ ID No: 20, SEQ ID No: 21, SEQ ID No: 22, and SEQ ID No: 23. In certain embodiments, the cleavage peptide 206 or 210 may have a sequence with greater than eighty percent (80%), eighty five percent (85%), ninety percent (90%), ninety five percent (95%), or ninety nine percent (99%) identity to a sequence selected from the group consisting of the SEQ ID No: 4, SEQ ID No: 5, SEQ ID No: 6, SEQ ID No: 7, SEQ ID No: 8, SEQ ID No: 20, SEQ ID No: 21, SEQ ID No: 22, and SEQ ID No: 23. The cleavage peptide 206 or 210 may also have other sequence that may be recognized by a protease specifically. The cleavage peptide 206 and 210 may be recognized by the same protease. The cleavage peptide 206 and 210 may be also recognized by different proteases.

For example, a peptide with a sequence of SEQ ID Nos: 21-23 may be recognized by a matrix metalloproteinase 9 (MMP9). MMP9 can be involved in inflammation associated with aortic aneurysms. doxycycline, and in the development of several human malignancies, cancers, such as breast cancers, colitis cancer, intestinal cancers, and other cancers. MMP9 may recognize and cleave a peptide with a sequence that is identical or similar to SEQ ID Nos: 21-23. When the expressed protein 202 delivered to certain cancers, the MMP9, which may be present in a cancer cell with high concentration, may react with the cleavage peptide 206 and/or 210 to release the protein 208.

Figure 3:
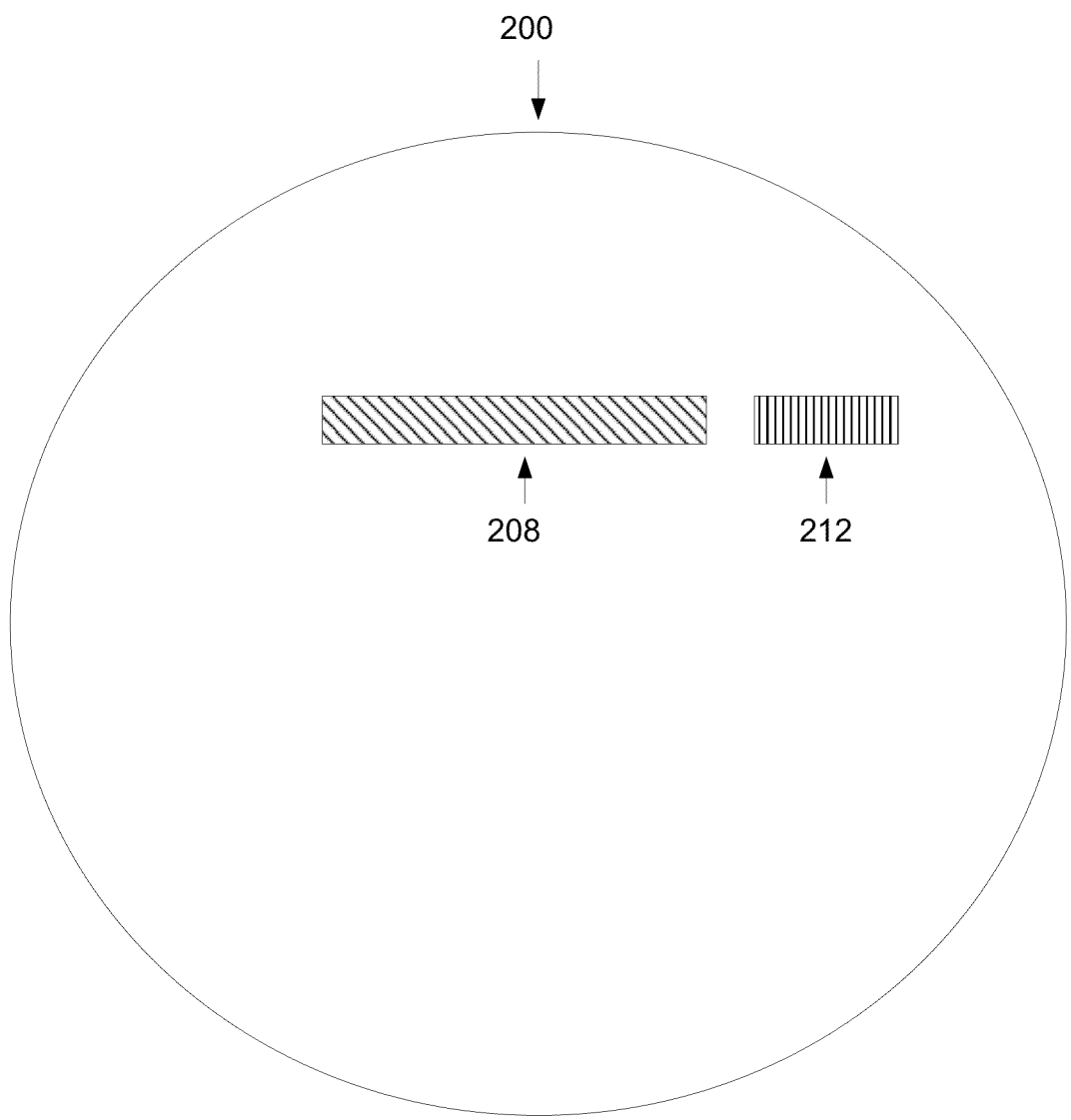
FIG. 3 illustrates an exemplary activation of an expressed protein consistent with the disclosed embodiments.

FIG. 3 illustrates an exemplary activation of the protein 208 consistent with the disclosed embodiments. As shown in FIG. 3, the target protein 208 may be created by enzymatic reaction to remove the target delivery peptide 204 and/or the marker protein 212. The enzymatic treatment to remove the peptide 204 and/or the protein 212 may occur inside the cell 200. The enzymatic treatment to remove the peptide 204 and/or the protein 212 may also occur outside the cell 200. The enzymatic treatment to remove the peptide 204 and/or the protein 212 may occur before the purification and/or isolation of the target protein 208. The enzymatic treatment to remove the peptide 204 and/or the protein 212 may also occur after the purification and/or isolation of the target protein 208. In certain embodiments, the removal of the tag 204 and/or the protein 212 may occur at the same cell where the recombinant protein 202 is produced. In certain embodiments, the recombinant protein 202 may be delivered to a location different to the cell producing the protein 202 and the tag 204 and/or the protein 212 may be removed after the delivery. In certain embodiments, the cells wherein the removal of the tag 204 and/or the protein 212 occurs may express the gene that encodes the proteases that recognizes and reacts on the cleavage peptide 206 and 210. In certain embodiments, the gene encoding the protease that recognizes and reacts on the cleavage peptide 206 and 210 may be introduced into the cells wherein the removal of the tag 204 and/or the protein 212 occurs. In certain embodiments, the protease recognizing and reacting on the cleavage peptide 206 and 210 may be introduced to remove the tag 204 and/or the protein 212.

Figure 4:
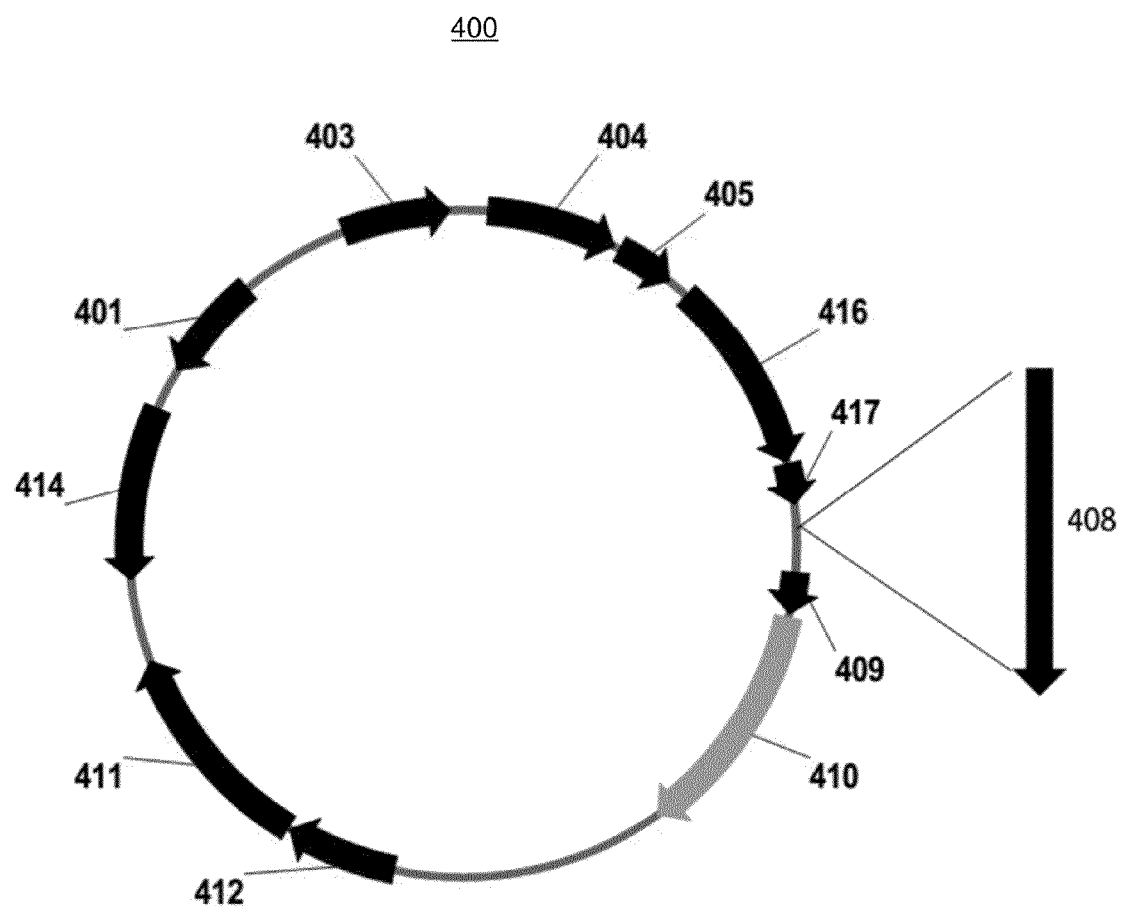
FIG. 4 illustrates an exemplary expression vector consistent with the disclosed embodiments.

FIG. 4 illustrates an exemplary vector 400 consistent with the disclosed embodiments. As shown in FIG. 4, the vector 400 may include a bacterial promoter 404, a signal peptide sequence 405, a tag sequence 416, and a first cleavage site 417. The vector 400 may further include a first replication origin 401, a first selective marker 414.

The promoter 404 may be a promoter that drives the expression of a gene in a bacterium. In certain embodiments, the promoter 404 may be a promoter as listed in Table 6, such as a T7 promoter. Other types of promoter may also be used. The promoter 404 may be derived from an organism, such as an animal, a plant, a bacterium, a eukaryotic microorganism, or a virus. The promoter 404 may also include one or more mutations to a sequence derived from an organism. The promoter 404 may also be artificially designed and/or synthesized.

TABLE 6

Promoters in Bacteria Expression Vector

TV: Promoter from TV Bacteriophage
Pdes: Temperature sensor promoter
lacUV5: lacUV5 promoter
lambda PR: lambda PR promoter
Synthesis Promoter: Any synthesized promoter The promoter 404 may be under the control of an expression regulating sequence 403. The expression regulation sequence 403 may respond to the change of the cell culture condition or other signals. The expression regulating sequence 403 may also direct the expression of the recombinant gene in a temporal or spatial specific manner. For example, the expression regulating sequence 403 may be responsive to temperature regulation, such as at lower temperature of 25° C. to induce expression of the protein or enzyme after cooling down from fermentation tank at high temperature in order to avoid protein degradation or denature during the procedure of fermentation/manufacture.

The expression regulating sequence 403 may be derived from an organism, such as an animal, a plant, a bacterium, a eukaryotic microorganism, or a virus. The expression regulating sequence 403 may also include one or more mutations to a sequence derived from an organism. The expression regulating sequence 403 may also be artificially designed and/or synthesized.

The vector 400 may include a sequence 405 encoding a signal peptide. The sequence 405 may be derived from an organism, such as an animal, a plant, a bacterium, a eukaryotic microorganism, or a virus. The sequence 405 may also include one or more mutations to a sequence derived from an organism. The sequence 405 may also be artificially designed and/or synthesized.

The tag sequence 416 may encode a peptide. In certain embodiments, the tag 416 may be a target delivery sequence. The target delivery sequence may encode a target delivery peptide that may direct the expressed protein to certain location, for example, nucleus, peroxisome, certain specific type of cells, extracellular matrix, or outside of the cell. The targeting delivery peptide encoded by the sequence 416 may direct the expressed protein to any appropriate locations. The tag sequence 416 may be similar to the tag sequence 105.

The vector 400 may further include a first cleavage site 417. The first cleavage site 417 may encode a peptide that is specifically recognized by a protease. After the expression of the recombinant gene, the tag 416 may be removed from the target protein by the protease digestion. In certain embodiment, the cleavage site 417 may be similar to the cleavage site 106.

A gene 408 may be introduced into the vector 400 through molecular cloning technique. For example, the gene 408 may be digested by a first restriction enzyme and a second restriction enzyme. The vector 400 may be digested by the first restriction enzyme and the second restriction enzyme. The digested gene 408 and vector 400 may be ligated by a ligase. In certain embodiments, the first selective marker 414 may be an ampicillin resistant gene. The marker 414 may also be other appropriate selective gene.

The vector 400 may further include a second cleavage site 409. The second cleavage site 409 may be similar to the first cleavage site 417. The second cleavage site 409 may be the same to the first cleavage site 417. That is, the cleavage sites 409 and 417 may have the identical sequence. The second cleavage site 409 may also be different to the first cleavage site 417. That is, the cleavage sites 409 and 417 may have different sequence.

The vector 400 may also include a marker gene 410. The marker gene 410 may be similar to the marker gene 112.

Figure 5:
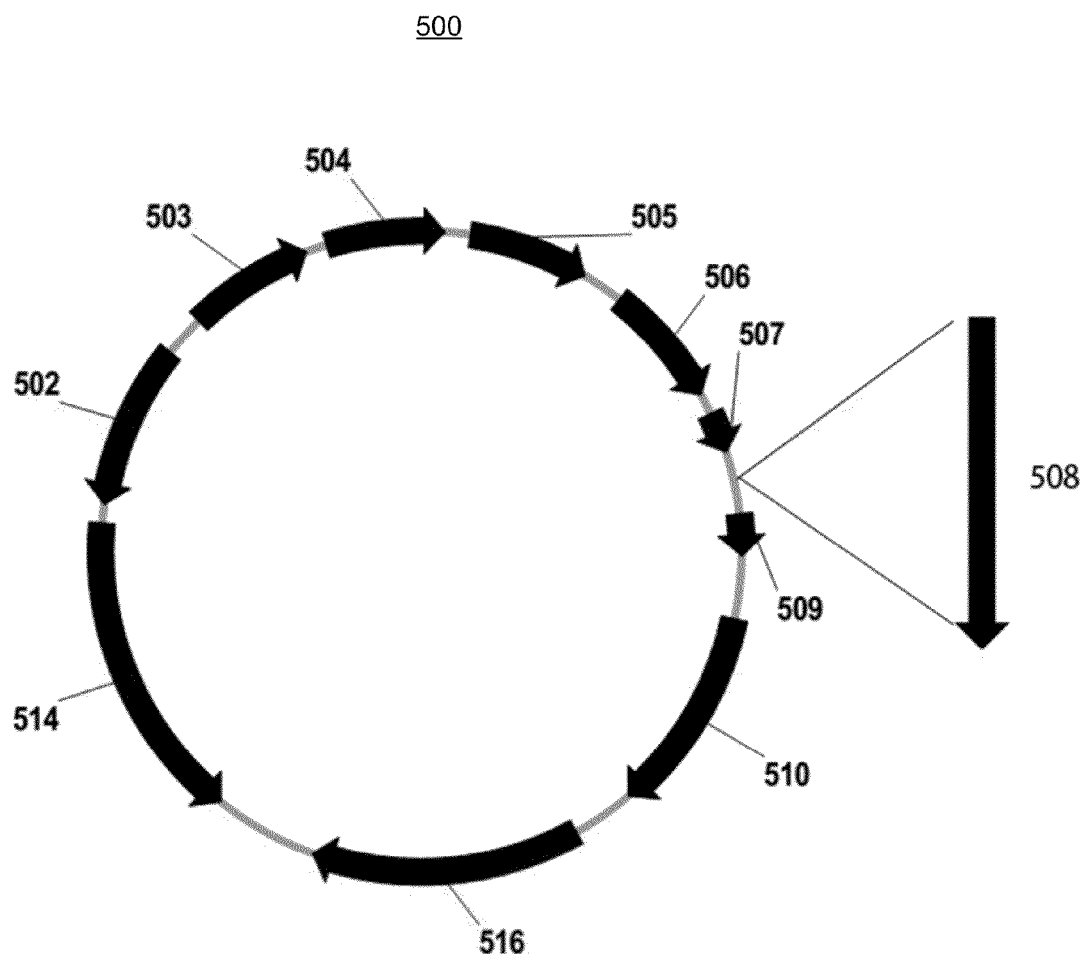
FIG. 5 illustrates an exemplary expression vector consistent with the disclosed embodiments.
Figure 6A:
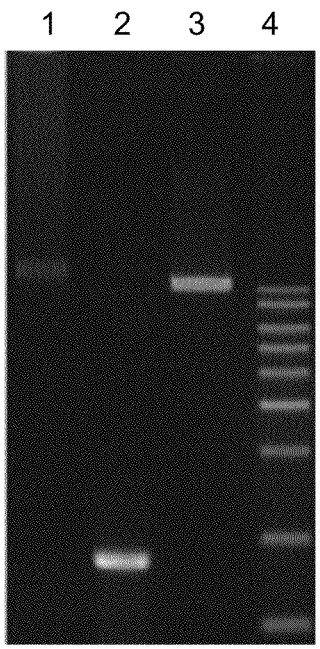
FIGS. 6A-6D illustrate gel electrophoresis analysis of exemplary expression vectors with insert transgene consistent with the disclosed embodiments.
Figure 6B:
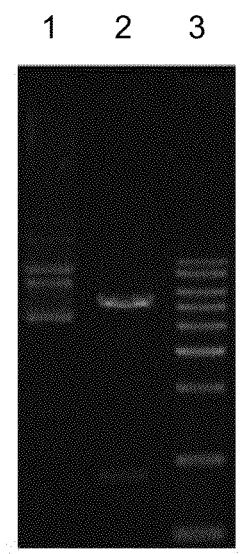
Figure 6C:
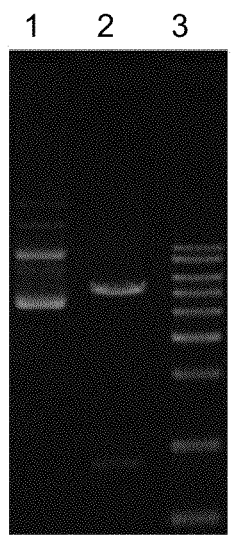
Figure 6D:
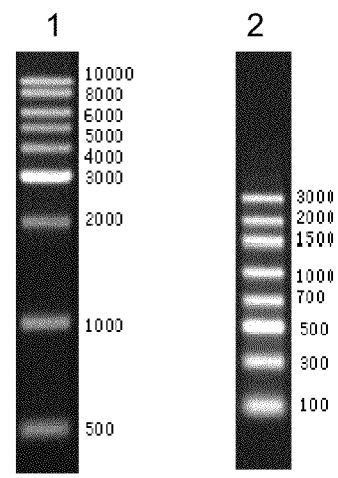

FIG. 5 illustrates an exemplary vector 500 consistent with the disclosed embodiments. As shown in FIG. 5, the vector 500 may include a promoter 504, a signal peptide sequence 505, a tag sequence 506, and a cleavage site 507. The vector 500 may further include a first replication origin 502, a first selective marker 514.

The promoter 504 may be a promoter that drives the expression of a gene in a yeast cell. In certain embodiments, the promoter 504 may be one of the promoters as listed in Table 7, such as AOX1, AOX2, CAG, TEF, and FLD1 promoter. Other types of promoter may also be used. The promoter 504 may be derived from an organism, such as an animal, a plant, a bacterium, a eukaryotic microorganism, or a virus. The promoter 504 may also include one or more mutations to a sequence derived from an organism. The promoter 504 may also be artificially designed and/or synthesized.

TABLE 7

Promoters in Yeast Expression Vector

TEF: TEF gene promoter
AOX1/AOX2: alcohol oxidase gene promoter, induceable by methanol
CAG: CAG Promoter
FLD1: FLD1 Promoter, induceable by methylamine
Synthesis promoter: Any synthesized promoter The promoter 504 may be under the control of an expression regulating sequence 503. The expression regulation sequence 503 may respond to the change of the cell culture condition or other signals. The expression regulating sequence 503 may also direct the expression of the recombinant gene in a temporal or spatial specific manner. For example, the expression regulating sequence 514 may be responsive to certain reagents, such as glucose, and induce the expression of the recombinant gene upon the addition of glucose in cell culture or without using harmful reagents such as the methanol, methylamine. The expression regulating sequence 514 may also be responsive to developmental signal in vivo.

The expression regulating sequence 503 may be derived from an organism, such as an animal, a plant, a bacterium, a eukaryotic microorganism, or a virus. The expression regulating sequence 503 may also include one or more mutations to a sequence derived from an organism. The expression regulating sequence 503 may also be artificially designed and/or synthesized.

The tag sequence 506 may encode a peptide. The tag sequence 506 may be similar to the tag sequence 105. The vector 500 may further include a first cleavage site 507. The first cleavage site 507 may be similar to the cleavage site 106.

A gene 508 may be introduced into the vector 500 through molecular cloning technique. For example, the gene 508 may be digested by a first restriction enzyme and a second restriction enzyme. The vector 500 may be digested by the same first restriction enzyme and the second restriction enzyme. The digested gene 508 and vector 500 may be ligated by a ligase.

The vector 500 may further include a second cleavage site 509. The second cleavage site 509 may encode a peptide that is specifically recognized by a protease. After the expression of the recombinant gene, a protease digestion may remove other peptide that is attached to the target protein at its C-terminus. The second cleavage site 509 may be similar to the first cleavage site 507. The second cleavage site 509 may be the same to the first cleavage site 507. That is, the cleavage sites 507 and 509 may have the identical sequence. The second cleavage site 509 may also be different to the first cleavage site 507. That is, the cleavage sites 507 and 509 may have different sequence.

The vector 500 may also include a marker gene 510. The marker gene 510 may be similar to the marker gene 112.

EXAMPLES

Example 1

Cloning and Sequence Analysis of Recombinant Expression Vector USVG-A

The structure of the vector USVA-A is similar to that of the vector 100. The Vector USVA-A includes a CMV promoter, a HIV-Tat/VP22 Tag, a first cleavage site with a sequence that is substantially identical to SEQ ID No: 9, a MCS, a second cleavage site with a sequence that is substantially identical to SEQ ID No: 9, and a GFP as a marker. The vector USVA-A is digested by NsiI and SmaI at 37° C. for 1.5-2 hours (Fermentas). A target gene A may be synthesized by PCR or isolated from a vector. The target gene A is also digested by NsiI and SmaI and is cloned into the digested USVG-A vector. In certain embodiment, the target gene A may have a nucleotide sequence substantially identical to SEQ ID No: 10 as shown in Table 8. The target gene A may encode a protein having a sequence with greater than eighty percent (80%), eighty five percent (85%), ninety percent (90%), ninety five percent (95%), or ninety nine percent (99%) identity to the sequence of SEQ ID No: 11. Thus, a protein encoded by the target gene A may exhibit similar biological activity of the protein encoded a gene with the sequence of SEQ ID No: 11. The sequence of the recombinant vector was analyzed.

TABLE 8

SEQ ID No: 10, DNA sequence of
Glucocerebrosidase from Homo sapiens
atggagtttt caagtccttc cagagaggaa tgtcccaagc
ctttgagtag ggtaagcatc atggctggca gcctcacagg
attgcttcta cttcaggcag tgtcgtgggc atcaggtgcc
cgcccctgca tccctaaaag cttcggctac agctcggtgg
tgtgtgtctg caatgccaca tactgtgact cctttgaccc
cccgaccttt cctgcccttg gtaccttcag ccgctatgag
agtacacgca gtgggcgacg gatggagctg agtatgggc
ccatccaggc taatcacacg ggcacaggcc tgctactgac
cctgcagcca gaacagaagt tccagaaagt gaagggattt
ggaggggcca tgacagatgc tgctgctctc aacatccttg
ccctgtcacc ccctgcccaa aatttgctac ttaaatcgta
cttctctgaa gaaggaatcg gatataacat catccgggta
cccatggcca gctgtgactt ctccatccgc acctacacct
atgcagacac ccctgatgat ttccagttgc acaacttcag
cctcccagag gaagatacca agctcaagat accccctgatt
caccgagccc tgcagttggc ccagcgtccc gtttcactcc
ttgccagccc ctggacatca cccacttggc tcaagaccaa
tggagcggtg aatgggaagg ggtcactcaa gggacagccc
ggagacatct accaccagac ctgggccaga tactttgtga
agttcctgga tgcctatgct gagcacaagt tacagttctg
ggcagtgaca gctgaaaatg agccttctgc tgggcgttg
agtggatacc ccttccagtg cctgggcttc accctgaac
atcagcgaga cttcattgcc cgtgacctag gtcctaccct
cgccaacagt actcaccaca atgtccgcct actcatgctg
gatgaccaac gcttgctgct gccccactgg gcaaaggtgg
tactgacaga cccagaagca gctaaatatg ttcatggcat
tgctgtacat tggtacctgg actttctggc tccagccaaa
gccaccctag gggagacaca ccgcctgttc cccaacacca
tgctctttgc ctcagaggcc tgtgtgggct ccaagttctg
ggagcagagt gtgcggctag gctcctggga tcgagggatg
cagtacagcc acagcatcat cacgaacctc ctgtaccatg
tggtcggctg gaccgactgg aaccttgccc tgaacccga
aggaggaccc aattgggtgc gtaactttgt cgacagtccc
atcattgtag acatcaccaa ggacacgttt acaaacagc
ccatgttcta ccaccttggc cacttcagca agttcattcc
tgagggctcc cagagagtgg ggctggttgc cagtcagaag
aacgacctgg acgcagtggc actgatgcat cccgatggct
ctgctgttgt ggtcgtgcta aaccgctcct ctaaggatgt
gcctcttacc atcaaggatc ctgctgtggg cttcctggag
acaatctcac ctggctactc cattcacacc tacctgtggc
gtcgccagtg gagcagatac tcaaggaggc actgggctca
gcctgggcat agggacagag tcagctcaca cgctgtctgt
gacagagggc acagcagggc cagtgtgagc ttacagcgac
gtaagcccag gggcaatggt ttgggtgact cactttcccc
tctaggcggt gcccagggc tggaggcccc tagaaaaaga
tcagtaagcc ccagtgtccc cccagccccc atgcttatga
catgcgctgt gtgctgcttg cttttggaaac tgggcctggg
tccaggccta ggggctcact gtccgtacaa acacaagatc
agggctgagg gtaaggaaaa gaagagacta ggaaagctgg
gcccaaaact ggagactgtt tgtctttcct ggagatgcag
aactgggccc gtggagcagc agtgtcagca tcagggcgga
agccttaaag cagcagcggg tgtgcccagg cacccagatg
attcctatgg caccagccag gaaaaatggc agctcttaaa
ggagaaaatg tttgagccc SEQ ID No: 11, Protein sequence of
Glucocerebrosidase from Homo sapiens
MEFSSPSREE CPKPLSRVSI MAGSLTGLLL LQAVSWASGA
RPCIPKSFGY SSVVCVCNAT YCDSFDPPTF PALGTFSRYE

TABLE 8-continued

```
STRSGRRMEL SMGPIQANHT GTGLLLTLQP EQKFQKVKGF
GGAMTDAAAL NILALSPPAQ NLLLKSYFSE EGIGYNIIRV
PMASCDFSIR TYTYADTPDD FQLHNFSLPE EDTKLKIPLI
HRALQLAQRP VSLLASPWTS PTWLKTNGAV NGKGSLKGQP
GDIYHQTWAR YFVKFLDAYA EHKLQFWAVT AENEPSAGLL
SGYPFQCLGF TPEHQRDFIA RDLGPTLANS THHNVRLLML
DDQRLLLPHW AKVVLTDPEA AKYVHGIAVH WYLDFLAPAK
ATLGETHRLF PNTMLFASEA CVGSKFWEQS VRLGSWDRGM
QYSHSIITNL LYHVVGWTDW NLALNPEGGP NWVRNFVDSP
IIVDITKDTF YKQPMFYHLG HFSKFIPEGS QRVGLVASQK
NDLDAVALMH PDGSAVVVVL NRSSKDVPLT IKDPAVGFLE
TISPGYSIHT YLWRRQWSRY SRRHWAQPGH RDRVSSHAVC
DRGHSRASVS LQRRKPRGNG LGDSLSPLGG AQGLEAPRKR
SVSPSVPPAP MLMTCAVCCL LWKLGLGPGL GAHCPYKHKI
RAEGKEKKRL GKLGPKLETV CLSWRCRTGP VEQQCQHQGG
SLKAAAGVPR HPDDSYGTSQ EKWQLLKEKM FEP
```

Example 2

Cloning and Sequence Analysis of Recombinant Expression Vector USVG-B

The USVG-B Vector has a structure similar to that of vector 400. The USVG-B includes a T7 promoter, a HIV-tat/22 tag, and a Thrombin cleavage site. A target gene B and the USVG-B were both digested using XhoI and KpnI. The digested target gene B and the USVG-B were ligated. The target gene B may have a nucleotide sequence substantially identical to SEQ ID No: 12 (Table 9). The target gene B may encode a protein having a sequence with greater than eighty percent (80%), eighty five percent (85%), ninety percent (90%), ninety five percent (95%), or ninety nine percent (99%) identity to the sequence of SEQ ID No: 13. Thus, a protein encoded by the target gene B may exhibit similar biological activity of the protein with the sequence of SEQ ID No: 13. The sequence of the recombinant vector was analyzed. The target gene B may also have a nucleotide sequence substantially identical to SEQ ID No: 14 (Table 10). The target gene B may encode a protein having a sequence with greater than eighty percent (80%), eighty five percent (85%), ninety percent (90%), ninety five percent (95%), or ninety nine percent (99%) identity to the sequence of SEQ ID No: 15. Thus a protein encoded by the target gene B may exhibit similar biological activity of the protein with the sequence of SEQ ID No: 15. The target gene B may also have a nucleotide sequence substantially identical to SEQ ID No: 16 (Table 11). The target gene B may encode a protein having a sequence with greater than eighty percent (80%), eighty five percent (85%), ninety percent (90%), ninety five percent (95%), or ninety nine percent (99%) identity to the sequence of SEQ ID No: 17. Thus, a protein encoded by the target gene B may exhibit similar biological activity of the protein with the sequence of SEQ ID No: 17. The target gene B may also have a nucleotide sequence substantially identical to SEQ ID No: 18 (Table 12). The target gene B may encode a protein having a sequence with greater than eighty percent (80%), eighty five percent (85%), ninety percent (90%), ninety five percent (95%), or ninety nine percent (99%) identity to the sequence of SEQ ID No: 19. Thus, a protein encoded by the target gene B may exhibit similar biological activity of the protein with the sequence of SEQ ID No: 19.

TABLE 9

```
SEQ ID No: 12, DNA sequence of alkaline
lipase from Proteus sp.
atgccaacta catatccaat tgttttagtt catggtctat
ctggttttga taatgtcgtc ggttatcctt attttatgg
catcgcggat gccttagaaa aggatggtca taaagttttt
actgcctctc tttcggcatt taacgctaat gaagttcgtg
gtgaacaact ttggggattg tgcaaaaagt tctcaaagaa
acgaaagcca aaaaagattt tggccatagc caaggaccat
cttgtcgtta tgttgctgca aaacatgcaa aaaatattgc
ttctgttacc tctattaatg gtgaccatgg ttcagagatt
gcagatttgg tacgacgtat tgtacgtaag gatagtgtgc
cagaatatat tgctgatgca gaagctattg gtactattat
tctacatttt caggtcatcg cagtccacaa gatgccgttg
ctgcattgga agcattaaca acaaatgtaa cgttaaagta
cccacaaggg ttacctgcca ttcgtggtgg aggagaagtt
gtaaatggcg tctactatta ttcatttggt tatattcaag
gtttgattgt tgggaaaggc aatctactgg atcctactca
tgcagcaatg cgtgtattaa gtgcattctt tacacaaaat
ggtttggtag gtcgtacaag tatgcggtta ggactgatag
attatgcaga tcatctggat atggtaaatc aggttgctgg
gttagtaggg cgtggagata ttgttgctat ttatacaaac
catgcgaatt ttttagcaag aaagcttta SEQ ID No: 13, Protein sequence of alkaline
lipase from Proteus sp.
MPTTYPIVLV HGLSGFDNVV GYPYFYGIAD ALEKDGHKVF
TASLSAFNAN EVRGEQLWGL CKKFSKKRKP KKILAIAKDH
LVVMLLQNMQ KILLLLPLLM VTMVQRLQIW YDVLYVRIVC
QNILLMQKLL VLLFYIFRSS QSTRCRCCIG SINNKCNVKV
PTRVTCHSWW RRSCKWRLLL FIWLYSRFDC WERQSTGSYS
CSNACIKCIL YTKWFGRSYK YAVRTDRLCR SSGYGKSGCW
VSRAWRYCCY LYKPCEFFSK KAL
```

TABLE 10

```
SEQ ID No: 14, DNA sequence of
eugenol synthase from Ocimum basilicum
atggaggaaa atgggatgaa aagcaagatt ttaatatttg
gagggacagg ttacattgga aatcacatgg tgaaaggaag
cctcaaatta gggcacccaa cttatgtttt cacaaggcct
aattcctcca agacaacccct tcttgatgag ttccaatcct
tgggtgccat catagtcaag ggagagttgg atgagcatga
gaaactagtt gagttgatga agaaagttga tgttgtcata
tctgcacttg cattcccaca aattcttgat cagttcaaga
tcttggaggc catcaaggtt gctgggaata ttaagaggtt
tctaccgtcg gattttgggg tcgaggagga cagaataaac
gcattgccgc cgttcgaagc actcatagag aggaagagga
tgatcagaag agccattgaa gaagcaaata ttccttacac
ttatgtgtct gcaaattgct ttgcatcata cttcatcaac
tacttgctcc gcccttatga tccaaaagat gagatcacgg
tttacggcac cggggaagct aagttcgcga tgaactacga
acaagacatc gggctctaca cgatcaaagt tgcaactgat
cctagagcat tgaatcgtgt ggtgatctac agaccatcaa
caaatatcat aacacagctc gagttgattt cgaggtggga
gaaaaaaatt gggaagaagt tcaaaaagat tcatgtcccc
gaagaagaaa ttgtgcccct cacaaaagaa ctgccggagc
ccgagaatat acccatagca atccttcact gtctcttcat
agacggagcg acgatgagtt atgatttcaa ggagaacgat
gtggaggctt caactctgta tccagagttg aagttcacca
cgatcgatga gctcctcgac attttcgtgc acgatcctcc
accgccggct tcagcagcat tt SEQ ID No: 15, Protein sequence of
eugenol synthase from Ocimum basilicum
MEENGMKSKI LIFGGTGYIG NHMVKGSLKL GHPTYVFTRP
NSSKTTLLDE FQSLGAIIVK GELDEHEKLV ELMKKVDVVI
SALAFPQILD QFKILEAIKV AGNIKRFLPS DFGVEEDRIN
ALPPFEALIE RKRMIRRAIE EANIPYTYVS ANCFASYFIN
YLLRPYDPKD EITVYGTGEA KFAMNYEQDI GLYTIKVATD
PRALNRVVIY RPSTNIITQL ELISRWEKKI GKKFKKIHVP
EEEIVALTKE LPEPENIPIA ILHCLFIDGA TMSYDFKEND
VEASTLYPEL KFTTIDELLD IFVHDPPPPA SAAF
```

TABLE 11

SEQ ID No: 16, DNA sequence of lipoxygenase from *Glycine max* atgacaggtg ggatgtttgg aaggaagggg caaaagataa
aggggacagt ggtgttgatg ccaaagaatg tgttggactt
caacgccata acctccgtcg gaaaaggcag tgctaaggac
accgccaccg atttcttggg caaaggcttg gacgcattag
gtcatgcagt tgatgctctc actgccttcg ctggccatag
catctccttg cagcttatca gtgctactca gactgatggt
agtggaaaag gaaaagttgg aaacgaagcc tatttggaaa
aacatcttcc gaccttgcca acgttgggag caaggcagga
agcattcgat attaactttg aatgggatgc tagttttgga
attccaggag cattttacat caaaaacttt atgactgatg
agtttttcct cgtcagtgtt aaactcgagg acattccaaa
ccatggaacc attaacttcg tttgtaactc atgggtttat
aacttcaaaa gttacaaaaa gaatcgcatt ttctttgtca
atgatacata tcttccgagt gctacaccag gtccactagt
taagtacaga caagaagaat tggaggtttt aagaggagat
ggaacaggga agcgcagaga ctttgacaga atctatgatt
atgatatcta taatgatttg ggcaatccag atggtggtga
tcctcgccca atcattggag gctctagcaa ctatccttac
cctcgcaggg ttagaaccgg tagagaaaag accaggaaag
atcccaacag tgagaaacca ggcgagatat atgttccaag
agatgaaaac ttcggtcact tgaagtcatc tgatttcctt
acatatggaa tcaaatcctt atctcagaac gtgatacctt
tgttcaaatc tataatattg aacttaaggg tcacatcgag
tgagttcgat agcttcgacg aagtgcgtgg tctctttgaa
ggtggaatca agctgccaac aaatatactg agccaaatta
gccccttacc agtcctcaag gaaatcttcc gcactgatgg
tgaaaatacc cttcaatttc caccacctca tgtaatcaga
gttagtaaat ctggatggat gactgatgat gagtttgcaa
gagagatgat tgctggtgta aatccaaatg taattcgtcg
tcttcaagag ttcccaccaa aaagcactct tgatcccgca
acctatggtg atcaaactag taccataaca aaacaacagt
tggagattaa cttgggtggg gtcacagtag aagaggcaat
tagtgctcac agattattca tattagatta ccatgatgca
ttcttcccgt atttgacgaa gataaacagc ctacctattg
caaaagctta tgccacaagg acaatcctgt tcttgaaaga
cgatggatct ttaaagccac ttgctatcga attaagcaag
cctgcaacag tgagtaaagt ggtgttgcct gcaacagaag
gtgttgagag tacaatttgg ttgttggcca aggctcatgt
cattgtgaat gactctggtt atcatcagct cataagccat
tggttaaata ctcatgcagt gatggagcca tttgccatag
caacaaacag gcatctcagt gtgcttcacc ccatttataa
acttctttat cctcactaca aggacacaat aaatatcaat
ggccttgcta ggcagtccct gattaacgca ggtggcatta
ttgagcaaac atttttgcct ggaaagtact ccattgaaat
gtcatcagtt gtttacaaga attgggtttt cactgaccaa
gcattaccag ctgatcttgt caagagagga ttggcagttg
aggatccctc tgccccacat ggtcttcgcc ttgtgataga
ggactaccct tatgctgttg atggacttga aatatgggat
gctattaaga catgggtcca tgagtatgtc tctgtgtatt
acccaacaaa tgcagcaatt caacaagaca ctgaacttca
agcatggtgg aaggaagttg tggagaaggg tcatggtgac
ttaaaagata agccttggtg gcctaaactg cagactgtgg
aggatctcat tcaatcctgc tctattatca tatggacagc
ttcggctctc catgcagctg ttaattttgg gcaataccct
tatggaggtt atatcgtgaa ccgtccaact ctagccagaa
ggtttatccc agaagaagga accaaagaat atgatgagat
ggtgaaggat cctcaaaagg catatctgag aacaatcaca
cccaagttcg agacccttat tgacatttca gtgatagaga
tattgtcaag gcatgcttct gatgaggtct accttggcca
aagggataat ccaaattgga ctacggattc aaaggcattg
gaagctttca aaaagtttgg aaacaaactg gcagaaattg
agggaaaaat cacacagagg aacaatgatc caagtctgaa
aagccgacat gggccagttc agcttccata cacattgctc
catcgttcaa gtgaggaagg gatgagtttc aaaggaattc
ccaacagtat ctccatc SEQ ID No: 17, Protein sequence of lipoxygenase from *Glycine max*

MTGGMFGRKG QKIKGTVVLM PKNVLDFNAI TSVGKGSAKD
TATDFLGKGL DALGHAVDAL TAFAGHSISL QLISATQTDG
SGKGKVGNEA YLEKHLPTLP TLGARQEAFD INFEWDASFG
IPGAFYIKNF MTDEFFLVSV KLEDIPNHGT INFVCNSWVY
NFKSYKKNRI FFVNDTYLPS ATPGPLVKYR QEELEVLRGD
GTGKRRDFDR IYDYDIYNDL GNPDGGDPRP IIGGSSNYPY
PRRVRTGREK TRKDPNSEKP GEIYVPRDEN FGHLKSSDFL
TYGIKSLSQN VIPLFKSIIL NLRVTSSEFD SFDEVRGLFE
GGIKLPTNIL SQISPLPVLK EIFRTDGENT LQFPPPHVIR
VSKSGWMTDD EFAREMIAGV NPNVIRRLQE FPPKSTLDPA

TABLE 11-continued

TYGDQTSTIT KQQLEINLGG VTVEEAISAH RLFILDYHDA
FFPYLTKINS LPIAKAYATR TILFLKDDGS LKPLAIELSK
PATVSKVVLP ATEGVESTIW LLAKAHVIVN DSGYHQLISH
WLNTHAVMEP FAIATNRHLS VLHPIYKLLY PHYKDTININ
GLARQSLINA GGIIEQTFLP GKYSIEMSSV VYKNWVFTDQ
ALPADLVKRG LAVEDPSAPH GLRLVIEDYP YAVDGLEIWD
AIKTWVHEYV SVYYPTNAAI QQDTELQAWW KEVVEKGHGD
LKDKPWWPKL QTVEDLIQSC SIIIWTASAL HAAVNFGQYP
YGGYIVNRPT LARRFIPEEG TKEYDEMVKD PQKAYLRTIT
PKFETLIDIS VIEILSRHAS DEVYLGQRDN PNWTTDSKAL
EAFKKFGNKL AEIEGKITQR NNDPSLKSRH GPVQLPYTLL
HRSSEEGMSF KGIPNSISI

TABLE 12

SEQ ID No: 18, DNA sequence of Aflatoxin-detoxifizyme from *Armillariella tabescens* atggccacca caactgtcca ccgggagcga ttcctggcag
ataagtctgc tcctttgtgt ggtatggata ttagaaagtc
atttgatcag ctcagctcta aggaaaagct ctacacgcat
tacgtgaccg aagcttcttg ggcgggcgca agaatcatcc
aggctcagtg gaccccgcag gcgacagatc tatatgatct
gttgatcctt acgttcagcg taaatggaaa gctcgccgac
ctgaatgccc ttaagacgtc gtcaggcctt tcagaggacg
attgggaggc cttgatacag tacacggtcc aggtattgag
caatcttgtc aactacaaga cgttcggatt tacgaagatc
attccccgcg tcgacgcaga aaagtttgag tcagtggtca
aagcctctag caacgcagac cagggctcgg cactattcac
caagttgaaa caacacatat atgcgctttc tcctgagtca
gcgctattca ttggcaaaag gaaggacggt cacgtatcaa
attactatct tggtgaacct gttggagatg ctgaggtcga
tgctatccag aatgtcgctg agaagttagg cgttgatatc
ctcaatactc gcgtgaagaa gaatggagcg ggtgattaca
cgctcttagt tgcctctgct aaaaccagtc caccctccgt
gcatgacttc caaatcgact caactccggc taaattgacg
attgagtatg gcgactacgc gtcatctcta acgaaggttg
tcgccgccct tcaggaggcc aaacagtata ccgcgaacga
tcatcaatca gcgatgatcg aaggctatgt caagtcgttc
aactcaggat caattccgga acacaaagct gcgtcaacag
aatgggtgaa agatattgga ccggttgtag agtcctacat
cgggttcgtc gaaacctatg tcgacccata tggcggacgc
gcggaatggg agggtttcac tgccatcgtc gacaagcagc
tgagtgcgaa gtacgaagca ttggttaacg gtgctcctaa
gttgatcaag agtcttccgt ggggaacgga cttcgaggtt
gacgtcttca ggaagccgga ctttactgcg ttggaagtcg
tatcatttgc aacaggaggt attcctgccg gaatcaatat
accaaactat tatgaagtcc gggaaagcac agggtttaag
aatgtttcgc tagcgaatat tttggcggcc aaggtaccaa
acgaggagtt aactttcatc catcctgatg acgtagaact
atataacgct tgggatagtc gcgcgtttga acttcaggtg
gccaaccacg aacttttggg tcatggctcc ggcaagcttt
tccaagaagg tgctgatggg aaactgaact tcgatcccga
aaaggtcata aaccctctga ctggaaagcc gataacttca
tggtataagc cagggcaaac gccggattct gttttaggcg
aagtgtcgtc gtcaatggaa gaatgtcggg cggagaccgt
agcgctctac ttggttagca acctcgatat tcttaaaatt
ttcaattacg tcgacaagca agacattgaa gatatccagt
acatcacgtt cttgcttatg gcccgcgctg gtctgcgggc
actagagttt tatgatccag ccaccaagaa gcacggacag
gcacatatgc aggccagaat gggcataacc cagtacctga
ttcaagctgg gattgcgaga cttgaattga tccaggatgc
caacggcgaa ctcgaaaact tatacgttcg ggttgaccgg
gagaaagtgt tgtccaaagg aaaggaggtt gttggtcaat
tgctgatcga actccaagtc cggaaaagta ccgcagacgg
caccggctcc cgagatttct acacaacgct gaccgaacca
atctctggat gggagggcaa gatccgagac atcgttttga
agaagaagct tcctcgaaaa atctttgtcc aacccaatac
atttgtcgtc aacggcgaag tccagctcaa agagtatcct
ttgacggctg ccggggtaat tgaaagtttc attgagagac
gattgtgtca gagccaattg acaaacattg atgaatgtag
taaacgtgat cgtagcgata agatgtattc aaataacaat
tctacccaa SEQ ID No: 19, Protein sequence of Aflatoxin-detoxifizyme from *Armillariella tabescens*

MATTTVHRER FLADKSAPLC GMDIRKSFDQ LSSKEKLYTH
YVTEASWAGA RIIQAQWTPQ ATDLYDLLIL TFSVNGKLAD

TABLE 12-continued

```
LNALKTSSGL SEDDWEALIQ YTVQVLSNLV NYKTFGFTKI
IPRVDAEKFE SVVKASSNAD QGSALFTKLK QHIYALSPES
ALFIGKRKDG HVSNYYLGEP VGDAEVDAIQ NVAEKLGVDI
LNTRVKKNGA GDYTLLVASA KTSPPSVHDF QIDSTPAKLT
IEYGDYASSL TKVVAALQEA KQYTANDHQS AMIEGYVKSF
NSGSIPEHKA ASTEWVKDIG PVVESYIGFV ETYVDPYGGR
AEWEGFTAIV DKQLSAKYEA LVNGAPKLIK SLPWGTDFEV
DVFRKPDFTA LEVVSFATGG IPAGINIPNY YEVRESTGFK
NVSLANILAA KVPNEELTFI HPDDVELYNA WDSRAFELQV
ANHELLGHGS GKLFQEGADG KLNFDPEKVI NPLTGKPITS
WYKPGQTPDS VLGEVSSSME ECRAETVALY LVSNLDILKI
FNYVDKQDIE DIQYITFLLM ARAGLRALEF YDPATKKHGQ
AHMQARMGIT QYLIQAGIAR LELIQDANGE LENLYVRVDR
EKVLSKGKEV VGQLLIELQV RKSTADGTGS RDFYTTLTEP
ISGWEGKIRD IVLKKKLPRK IFVQPNTFVV NGEVQLKEYP
LTAAGVIESF IERRLCQSQL TNIDECSKRD RSDKMYSNNN
STQ
```

Example 3

Cloning and Sequence Analysis of Recombinant Expression Vector USVG-C

The USVG-C vector has a structure similar to that of vector 500. The USVG-C includes an AOX1 promoter, a HIV-tat/22 tag, and a Thrombin cleavage site. The target gene B, and the USVG-C were both digested using XhoI and KpnI. The digested target gene B and the USVG-C were ligated. The target gene B may be similar to those target genes B as describe above.

Example 4

Analysis of Transgene Insertion into a Vector

FIGS. 6A-6D illustrate gel electrophoresis analysis of exemplary expression vectors with insert transgene consistent with the disclosed embodiments. As shown in FIG. 6A, a USVG-A plasmid with a transgene insert was loaded on lane 1. A product of a PCR reaction, which was designed to detect the insertion of a transgene in the USVG-A plasmid, was loaded on lane 2. A restriction enzyme digestion product of the USVG-A plasmid was loaded on lane 3. A molecular weight marker was loaded on lane 4. After agarose gel electrophoresis, the result showed the insertion of transgene.

As shown in FIG. 6B, a USVG-B plasmid with a transgene insert was loaded on lane 1. A restriction enzyme digestion product of the USVG-B plasmid was loaded on lane 2. A molecular weight marker was loaded on lane 4. After agarose gel electrophoresis, the result showed the insertion of transgene.

As shown in FIG. 6C, a USVG-C plasmid with a transgene insert was loaded on lane 1. A restriction enzyme digestion product of the USVG-C plasmid was loaded on lane 2. A molecular weight marker was loaded on lane 4. After agarose gel electrophoresis, the result showed the insertion of transgene.

FIG. 4 shows the molecular weight marker used in FIGS. 6A-6C to measure the size of the DNA fragment on the agarose gel.

Example 5

Establishment of Stable Cell Lines

Cells were diluted at 1:10 or higher percentage into fresh growth medium 24 hours after transfection. Selective medium (if desired) was added the following day. The survival cell clones are isolated for repopulation in vitro.

Example 6

Expression and Isolation of Target Protein in Bacteria

The USVG-B with target gene B was expressed in bacterial cells. For bench scale expression and production of the protein used in the mouse immunogenicity studies, *E. coli* cells BL21 (DE3) or *B. subtilis* were transformed. Transformed cells were cultured overnight in 3 ml medium and overnight culture was used to inoculate 1 L of Luria-Bertani Broth (LB Broth). The cells then grew at 37° C. in a rotating shaker at 250 rpm until the optical density of the bacterial culture reached 0.6 at the wavelength of 600 nm. Isopropyl-d-1-thiogalactopyranoside (IPTG) was added to the culture to a final concentration of 1 mM to induce the expression of the recombinant enzymes. After 3 hours of induction, the supernatant of the culture was harvested by centrifugation, from which the enzyme encoded by target gene B was purified using one step of hydrophobic interaction chromatography (Phenyl Sepharose 6 Fast Flow, GE Healthcare, Piscataway, N.J.) and two steps of anion exchange (DEAE Sepharose Fast Flow and SOURCE 30Q, GE Healthcare, Piscataway, N.J.).

For scale up and large-scale production of enzymes, the *E. coli* production clone was fermented with in 5 L bioreactors. Fermentation broth was harvested using continuous centrifugation at 12,000 g and clarified supernatant was further processed by microfiltration using filter with molecular weight cut off (MWCO) at 750,000 Dalton, size 5 (UFP-750-E-5, GE Healthcare, Piscataway, N.J.).

After the filtration, the supernatant was further processed using ultrafiltration/diafiltration (UF/DF) cartridge with MWCO at 100,000 Dalton, size 5, (UFP-10-C-5, GE Healthcare) as suggested by the manufacturer. The UF/DF buffer consisted of 20 mM Tris-HCl, 100 mM NaCl, pH 7.2. Diafiltered and concentrated fermentation bulk was stored at −80° C. The fermentation bulk was thawed at 4° C. and diluted with water until the conductivity of the diluted solution was less than 5 mS/cm. The pH value of the diluted solution was adjusted to 5.9±0.2. The diluted solution was filtered using a 0.8-0.45 μm filter. The expressed protein was captured using a Capto Q column (GE Healthcare, Piscataway, N.J.). For each milliliter of resin, about 5 milligram of enzyme was loaded. The linear flow rate was between 300-400 cm/h. The impurities were removed by washing the column with a buffer consisting of 20 mM Bis-Tris, 150 mM NaCl, pH 5.9. The target enzyme protein was eluted with a buffer consisting of 20 mM Bis-Tris, 500 mM NaCl, pH 5.9.

Alternatively, the standard method of His-Tag protein purification column may be used to remove undesired proteins. The protein solution was diluted with 3.6M ammonium sulfate to a final concentration of 0.9M ammonium sulfate, pH 7.4. A Phenyl Sepharose HP column (GE Healthcare, Piscataway, N.J.) was equilibrated with a buffer consisting of 20 mM Tris-HCl, 0.9M ammonium sulfate, pH 7.4 prior to the sample being loaded at a linear flow of 100 cm/h. Recombinant protein was eluted with a buffer consisting of 20 mM Tris-HCl, pH 7.4 and diluted with water until the conductivity of the solution was less than 5 mS/cm. The pH of the eluted solution was adjusted to 6.5 prior to loading on a Q Sepharose Fast Flow column (GE Healthcare, Piscataway, N.J.) equilibrated with a buffer consisting of 20 mM Tris-HCl, pH 6.5 at a linear flow of 100 cm/h. Recombinant protein was eluted with a buffer consisting of 20 mM Tris-HCl, 250 mM NaCl, pH 6.5. The eluted recombinant protein solution was loaded on a Superdex 75 column (60 cm height, GE Healthcare, Piscataway, N.J.) equilibrated with saline such that the load volume did not exceed 6% of a column volume. The fraction containing gel permeation elution peak was collected and the concentration was determined by measuring the absorbance of the solution at the wavelength of 280 nm. Enzyme was biochemically characterized by amino-terminal sequencing, electro-spray ionization mass spectrometry, and reverse-phase HPLC. The purified recombinant protein may be further processed by application of specific reagent, which may remove the tag and release or yield the final purified protein.

Example 7

Western Blot to Detect the Gene Expression

The cells were prepared to form a cell suspension. The suspension was then transferred into 2 ml tube and centrifuged at 3,000 rpm and 4° C. for 5 min. After resuspending the cells pellets by buffer containing proteinase inhibitor, the reaction mix was placed on ice for 15 minutes and centrifuged at 20,000 g and 4° C. for 20 minutes. The supernatant containing protein was collected and chilled in liquid nitrogen and stored at −80° C. for later use. Twenty five microgram of protein from each sample was mixed with 5× loading buffer and 2-mercaptoethanol (5% of loading buffer). The mixture was boiled at 95° C. for 5 minutes to denature the protein. The denatured protein was then added into Criterion™ precast gel for electrophoresis at 200 volts for 50 minutes.

After the electrophoresis, the gel was placed in ice-cold transfer buffer for 3 min to equilibrate. A PVDF transfer membranes was cut into appropriate size and soaked in methanol for 2 min. The gel and PVDF transfer member were then sandwiched between sponge and paper after ensuring no air bubbles formed between the layers. The sandwich was submerged into pre-chilled transfer buffer at 100 volts for 1 hour. The member was rinsed for 5 minutes in buffer solution at room temperature. The member was then incubated with a primary antibody, which specifically recognizes the target protein, at 4° C. overnight. After overnight incubation, the membrane was then incubated with secondary antibody at room temperature for 1 hour. Thereafter, the membrane was rinsed in buffer solution. The membrane was then incubated with SuperSignal™ Chemiluminescent Substrate for signal detection. X-ray films and automated x-ray developer were used.

Example 8

Statistical Analysis

To test for a significant level of enhancement of antibody responses, a Kruskal-Wallis One-Way ANOVA was performed. The enhancement was considered to be significant when P-values of Kruskal-Wallis test is less than 0.025 were considered. If the Kruskal-Wallis test was significant, then a post hoc analysis was performed using Student-Newman-Keuls pairwise comparison with the P-values less than 0.05 considered significant. The effect of antigen dose on antibody response was tested by Spearman Rank Correlation one day 42. A dose response requires a p-value greater than 0 and P-value smaller than 0.05.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications. For example, other genes may be inserted into the expression vector for expression.

What is claimed is:

1. An expression vector for amplified expression of a transgene in a cell, comprising:
   a promoter configured to drive the expression of the transgene in the cell;
   a tag sequence encoding a tag peptide directing the protein of the expressed transgene to a pre-determined location;
   a first cleavage sequence encoding a peptide that is recognizable by a protease; and
   a marker gene configured to encoding a protein to indicate the expression of the transgene, wherein the transgene sequence encodes a protein having an amino acid sequence selected from the group consisting of SEQ ID NO:11, SEQ ID NO:13, and SEQ ID No: 19.

2. The expression vector of claim 1, wherein: the cell is a mammalian cell, and the promoter is a promoter configured to drive the expression of the transgene in the mammalian cell.

3. The expression vector of claim 2, wherein: the promoter is a cytomegalovirus (CMV) promoter, and the marker gene encodes a fluorescent protein.

4. The expression vector of claim 1, wherein:
   the tag sequence encodes a peptide with a sequence that is identical to a sequence selected from the group consisting of the SEQ ID No: 1, SEQ ID No: 2, SEQ ID No: 3, SEQ ID No: 24, and SEQ ID No: 25.

5. The expression vector of claim 1, wherein: the first cleavage sequence encoding a peptide having the sequence identical to a sequence selected from the group consisting of SEQ ID No: 4, SEQ ID No: 5, SEQ ID No: 6, SEQ ID No: 7, SEQ ID No: 8, SEQ ID No: 20, SEQ ID No: 21, SEQ ID No: 22, and SEQ ID No: 23.

6. The expression vector of claim 1, wherein: the cell is a bacterial cell and the promoter is a promoter configured to drive the expression of the transgene in the bacterial cell.

7. The expression vector of claim 6, wherein: the promoter is T7 promoter.

8. The expression vector of claim 6, wherein: the tag sequence encodes a peptide with a sequence that is identical to a sequence selected from the group consisting of the SEQ ID No: 1, SEQ ID No: 2, SEQ ID No: 3, SEQ ID No: 24, and SEQ ID No: 25.

9. The expression vector of claim 6, wherein: the first cleavage sequence encoding a peptide having the sequence identical to a sequence selected from the group consisting of SEQ ID No: 4, SEQ ID No: 5, SEQ ID No: 6, SEQ ID No: 7, SEQ ID No: 8, SEQ ID No: 20, SEQ ID No: 21, SEQ ID No: 22, and SEQ ID No: 23.

10. The expression vector of claim 1, wherein: the cell is a yeast cell and the promoter is a promoter configured to drive the expression of the transgene in the yeast cell.

11. The expression vector of claim 10, wherein: the promoter is an AOX1 promoter.

12. The expression vector of claim 10, wherein: the tag sequence encodes a peptide with a sequence that is identical to a sequence selected from the group consisting of the SEQ ID No: 1, SEQ ID No: 2, SEQ ID No: 3, SEQ ID No: 24, and SEQ ID No: 25.

13. The expression vector of claim 10, wherein: the first cleavage sequence encoding a peptide having the sequence identical to a sequence selected from the group consisting of the SEQ ID No: 4, SEQ ID No: 5, SEQ ID No: 6, SEQ ID No: 7, SEQ ID No: 8, SEQ ID No: 20, SEQ ID No: 21, SEQ ID No: 22, and SEQ ID No: 23.

14. The expression vector of claim 1, wherein: the promoter is located upstream to the tag sequence, the tag sequence is located upstream to the first cleavage sequence, the first cleavage sequence is located upstream to the transgene, and the transgene is located upstream to the marker gene.

15. A process for preparation of proteins using a vector having a promoter configured to drive the expression of a transgene in the cell, a tag sequence encoding a tag peptide performing a function of facilitating the protein of the expressed transgene and locating the protein of the expressed transgene to a pre-determined location, a cleavage sequence encoding a peptide that is recognizable by a protease a multiple cloning site (MCS) including sequence recognizable by a restriction enzyme, and a marker gene configured to encoding a protein to indicate the expression of the transgene, comprising the steps of:
    inserting the transgene into the MCS site of the expression vector;
    introducing the vector having the transgene into a cell;
    culturing the cell; and
    expressing the transgene in the cell, wherein the transgene sequence encodes a protein having an amino acid sequence selected from the group consisting of SEQ ID NO:11, SEQ ID NO:13, and SEQ ID No: 19.

* * * * *